(12) United States Patent
Laguna

(10) Patent No.: US 8,808,360 B2
(45) Date of Patent: Aug. 19, 2014

(54) APPARATUS AND METHODS FOR CONDUITS AND MATERIALS

(71) Applicant: Sentient Holdings, LLC, Flagstaff, AZ (US)

(72) Inventor: Alvaro J. Laguna, Flagstaff, AZ (US)

(73) Assignee: DSM IP Assets B.V. (NL)

( * ) Notice: Subject to any disclaimer, the term of this patent is extended or adjusted under 35 U.S.C. 154(b) by 0 days.

(21) Appl. No.: 13/748,061

(22) Filed: Jan. 23, 2013

(65) Prior Publication Data

US 2013/0133815 A1 May 30, 2013

Related U.S. Application Data

(60) Division of application No. 12/951,433, filed on Nov. 22, 2010, and a continuation-in-part of application No. 11/199,717, filed on Aug. 9, 2005, which is a continuation of application No. 10/071,635, filed on Feb. 7, 2002, now Pat. No. 6,949,121.

(60) Provisional application No. 61/265,527, filed on Dec. 1, 2009.

(51) Int. Cl.
*A61F 2/06* (2013.01)

(52) U.S. Cl.
USPC ....... 623/1.35; 623/1.36; 623/1.37; 623/1.38; 623/1.39; 623/1.11; 623/1.23; 623/1.15; 606/108; 606/194; 606/195; 606/198

(58) Field of Classification Search
USPC .......... 623/1.11, 1.12, 1.13, 1.14, 1.15, 1.35, 623/1.36, 1.37, 1.38, 1.39; 606/108, 194, 606/195, 198
See application file for complete search history.

(56) References Cited

U.S. PATENT DOCUMENTS 6,336,937 B1 * 1/2002 Vonesh et al. ................ 623/1.13

* cited by examiner

*Primary Examiner* — Vy Q Bui
(74) *Attorney, Agent, or Firm* — Greenberg Traurig, LLP

(57) ABSTRACT

The present invention provides apparatus and methods for a conduit, such as an implantable conduit for a vessel. The conduit may comprise a main member and a side-branch member. The conduit may be implanted with the side-branch member initially disposed within the main member. When positioned, the side-branch member may then be extended from within the main member and into a vessel side-branch. The materials for the conduit may include circumferentially distensible and/or low recoil materials. The materials for the conduit may be constructed by various techniques and may include materials with enhanced flexibility and kink resistance.

21 Claims, 13 Drawing Sheets

APPARATUS AND METHODS FOR CONDUITS AND MATERIALS

RELATED APPLICATION INFORMATION

This application is a divisional of U.S. application Ser. No. 12/951,433, filed on Nov. 22, 2010, which application claims the benefit of U.S. Provisional Application No. 61/265,527, filed on Dec. 1, 2009, and which also claims the benefit of and is a continuation-in-part of U.S. application Ser. No. 11/199,717, filed on Aug. 9, 2005, which application is a continuation of U.S. application Ser. No. 10/071,635, filed on Feb. 7, 2002 (now U.S. Pat. No. 6,949,121), each of which is incorporated herein by reference in its entirety.

BACKGROUND

The following disclosure generally relates to medical devices.

Vascular disease, the disease of blood vessels, is one of the leading causes of death in the western world. There are two main categories of vascular disease, aneurysmal and occlusive. Aneurysmal disease results in the weakening of blood vessels causing them to dilate excessively and in some instances ultimately rupture. Occlusive disease results in blockage of blood vessels, limiting the conveyance of blood.

Stents and stent-grafts are commonly used to treat diseased blood vessels and other tubular structures within the body. Stents and stent-grafts have been employed successfully to either reinforce afflicted blood vessels in the case of aneurysmal disease, or to radially open and support blood vessels for the purpose of restoring blood flow in the case of occlusive disease. To such ends, stents and stent-grafts have been implanted in the coronary as well as peripheral vasculature. Additionally, stents have been implanted within the neurovasculature, and in other bodily conduits such as the urinary tract, the bile duct, and the tracheo-bronchial tree.

Current stent-grafts intended for the treatment of aneurysmal disease are generally available in various diameters. Several devices are available in bifurcated configurations. These bifurcated devices are typically designed for use within the aortic bifurcation, where the abdominal aorta branches into the right and left common iliac arteries. Frequently, this anatomic region is riddled by aneurysmal disease, causing a potentially life-threatening situation. In an effort to treat the potentially life-threatening situation, bifurcated stent-grafts are implanted within the aneurysmal regions of the afflicted vessels, essentially forming a new blood flow conduit within the aneurysm, and isolating the aneurysm from blood flow and the associated blood pressure. This is referred to as excluding the aneurysm. Similarly, aneurysms of the aortic arch and the thoracic aorta are also common.

Conventional stent-grafts, however, do not accommodate side-branches of the aorta. Once an aneurysm has been excluded, the entire diseased section of the afflicted vessel is isolated from normal blood flow. This isolation includes any side-branches emanating from the aorta within the afflicted region. While this may be a good outcome from the perspective of managing a potentially life-threatening situation, such isolation from blood flow can lead to ischemic complications in certain areas of the body. For example, emanating from the abdominal aorta distal to the renal arteries are lumbar arteries, testicular/ovarian arteries, and the inferior mesenteric artery, which provides blood to the left transverse colon, descending and sigmoid colons, and rectum. Many aneurysms of the abdominal aorta include the origin of the inferior mesenteric artery. After successful exclusion of these aneurysms, the left transverse colon, descending and sigmoid colons, and rectum rely on collateral circulation for their blood supply. For many patients, the collateral circulation is sufficient, but for others it is not, resulting in complications involving the various organs.

Additionally, many aorto-iliac aneurysms involve the abdominal aorta as well as substantial portions of either (or both) of the common iliac arteries. In many cases, the disease extends along the common iliac artery past the bifurcation point where the common iliac branches into the external and the internal iliac arteries. In such cases, the endoluminal treatment of the aneurysm may require extending the stent-graft device into the external iliac artery, isolating the internal iliac artery from normal blood supply and leaving large portions of the pelvic area and leg reliant on collateral circulation for their blood supply. For example, the hypogastric artery, which supplies blood to the pelvic area, branches from the internal iliac artery. Isolation of the hypogastric artery from normal blood flow can result in buttock claudication, impotence, and colon ischemia.

Aneurysms of the aortic arch, for example, can be especially difficult to treat using currently available stent-graft devices. Three major vessels originate from the aortic arch: the brachiocephalic, the left common carotid, and the subclavian artery. These vessels provide critical blood flow to the head, neck and arms. If a stent-graft device is endoluminally implanted to treat aortic arch aneurysms, adjunctive measures must be taken to ensure adequate blood supply to the body parts (especially the brain) that receive their blood supply from the affected vessels.

On the other hand, while in some instances isolation of a side-branch vessel via aneurysm exclusion results in compromised blood supply due to inadequate collateral circulation, in situations of abundant collateral circulation, the presence of a side-branch vessel can actually hinder aneurysm exclusion. Retrograde blood flow from side-branches emanating within the aneurysmal region can maintain blood pressure within the aneurysm, often resulting in leakage between the stent-graft device and the afflicted vessel.

Like stent-grafts intended for the treatment of aneurysmal disease, stent-grafts intended for the treatment of occlusive disease are generally tubular and available in various diameters. Such stent-graft devices offer the advantage of providing a physical barrier, which impedes reproliferation of the disease through the wall of the implanted device. The treatment of vessels afflicted by occlusive disease at points of bifurcations, however, can be problematic due to the unpredictability of the vascular remodeling associated with balloon angioplasty and stent-graft implantation. In many instances, side-branches can be compromised as a result of plaque redistribution from the main vessel into the origin of the side-branch, resulting in stenosis of the side-branch.

SUMMARY

A prosthetic conduit according to various described embodiments includes a main member and a side-branch member. The main member may be configured to reside in a main vessel. For example, one embodiment comprises at least one stent, at least one main graft, and at least one opening in its side wall. The side-branch member is suitably configured to reside in a side-branch vessel, and may include, for example, at least one side-branch stent and at least one side-branch graft. The side-branch member is connected to the main member at the side wall opening. The side-branch member may be configured to be extendable through the opening to deploy the stent-graft.

The side-branch member may be located within the main member before and during delivery of the stent-graft to a desired location within a vessel. Once the main member is placed in a desired location, the side-branch member may be pushed or pulled out of the main member and into the desired side-branch vessel. The stent-graft may be inserted into a vessel at one access site and placed at a desired location within the vessel by any suitable method, such as using balloon catheters, guidewires, and/or a constraining sheath with a push tube.

Materials according to various aspects of the described embodiments that may be used in the main member, the side-branch member, and/or other elements are distensible. In this regard, exemplary embodiments provide characteristics such as enhanced flexibility, kink resistance, and/or limited foreshortening. By way of example only, the materials may be treated to circumferentially distend without significant foreshortening and/or recoil while other forms of manipulation may be employed to impart improved flexibility.

BRIEF DESCRIPTION OF THE EXEMPLARY DRAWINGS

Additional aspects of the disclosed embodiments will become evident upon reviewing the non-limiting descriptions set forth in the specification and claims, in conjunction with the accompanying figures, wherein like numerals designate like elements and wherein:

Figure 14A:
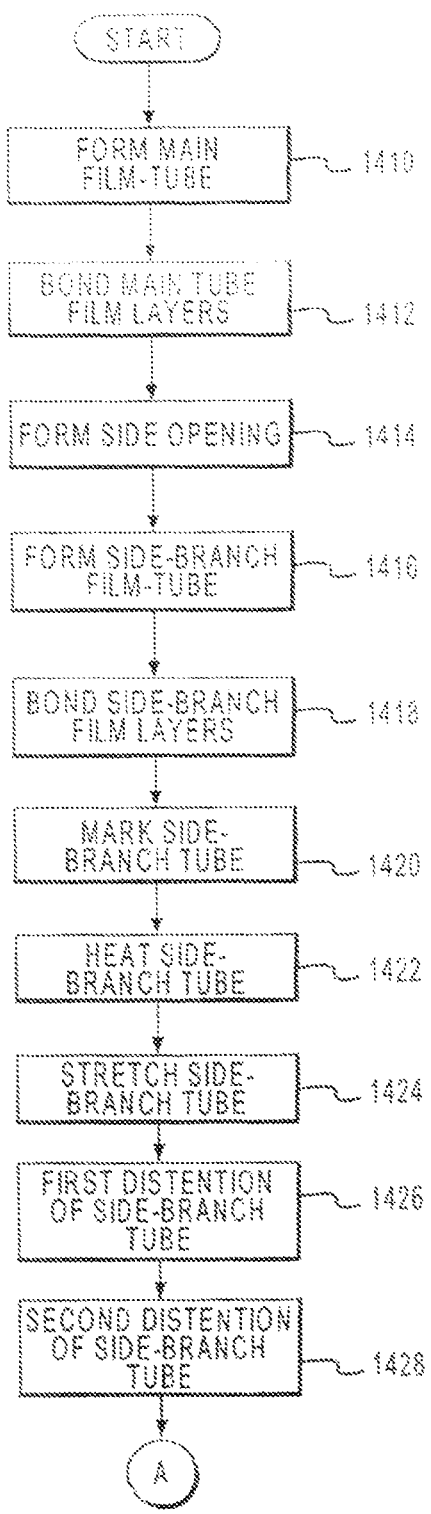
Figure 14B:
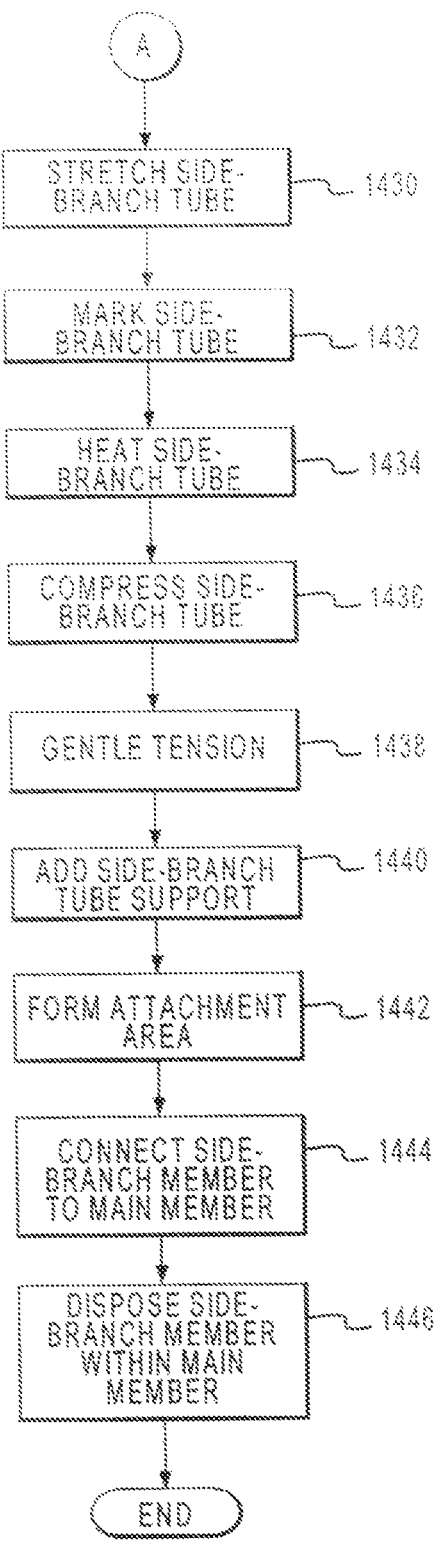

FIGS. 14A-B are a flow chart illustrating an exemplary preparation process for a prosthetic conduit.

Figure 15:
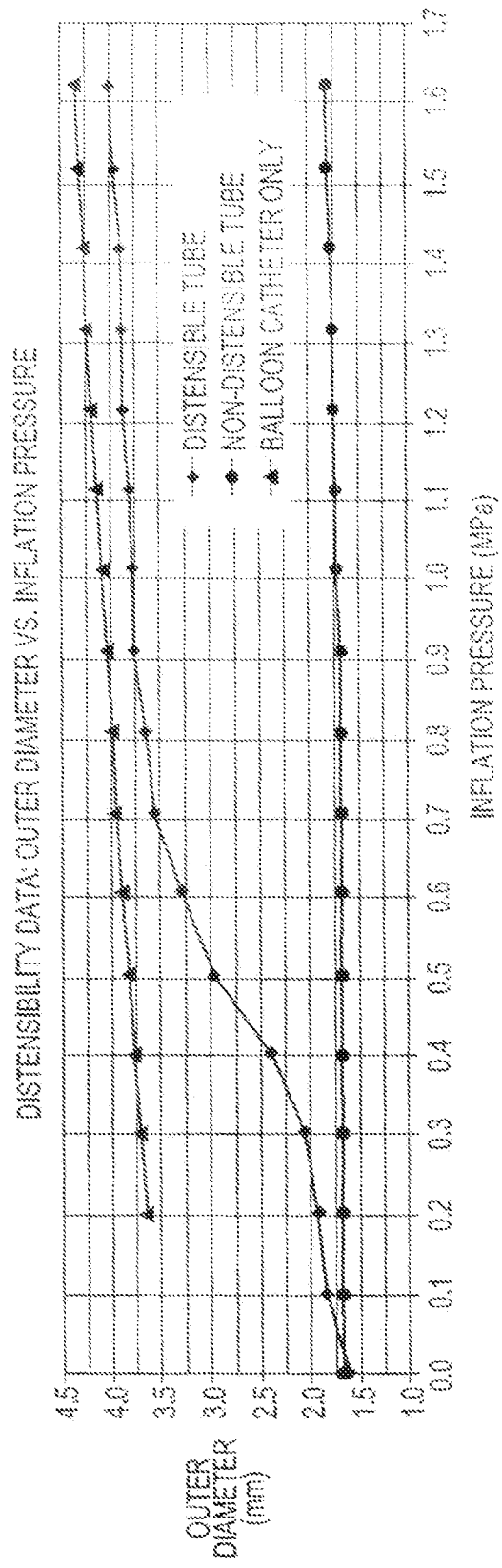

FIG. 15 is a graph illustrating distensibility data for a distensible tube and a non-distensible tube.

It is to be noted that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Various aspects and features disclosed hereinafter may be described in terms of functional components and steps. Such functional components and steps may be realized by any number of elements and/or steps configured to perform the specified functions. For example, the present methods and apparatus may employ conduits and supports, like grafts and stents, which may carry out a variety of functions in various embodiments, applications, and environments. In addition, the present methods and apparatus may be practiced in conjunction with any number of procedures and systems, and the apparatus and methods described are merely exemplary applications. Further, the present methods and apparatus may employ any number of techniques, conventional or otherwise, for placement, use, manufacturing, and the like. Such general techniques that may be referred to are not described in detail.

A prosthetic conduit system according to various aspects of the disclosed embodiments is implantable within an organism, such as a human being or animal. The prosthetic conduit may comprise any conduit, for example for use in blood vessels, bile ducts, the urinary tracts, or any other conduit in the organism. For example, a prosthetic blood vessel structure may comprise a stent, a graft, a stent-graft, or other implantable structure. The prosthetic blood vessel may be configured, however, in any manner according to the particular application or environment, including variations in dimensions, shape, materials, flexibility, and the like. Various aspects of the disclosed embodiments may also be applicable to other devices, such as other medical devices and other conduits.

Figure 1:
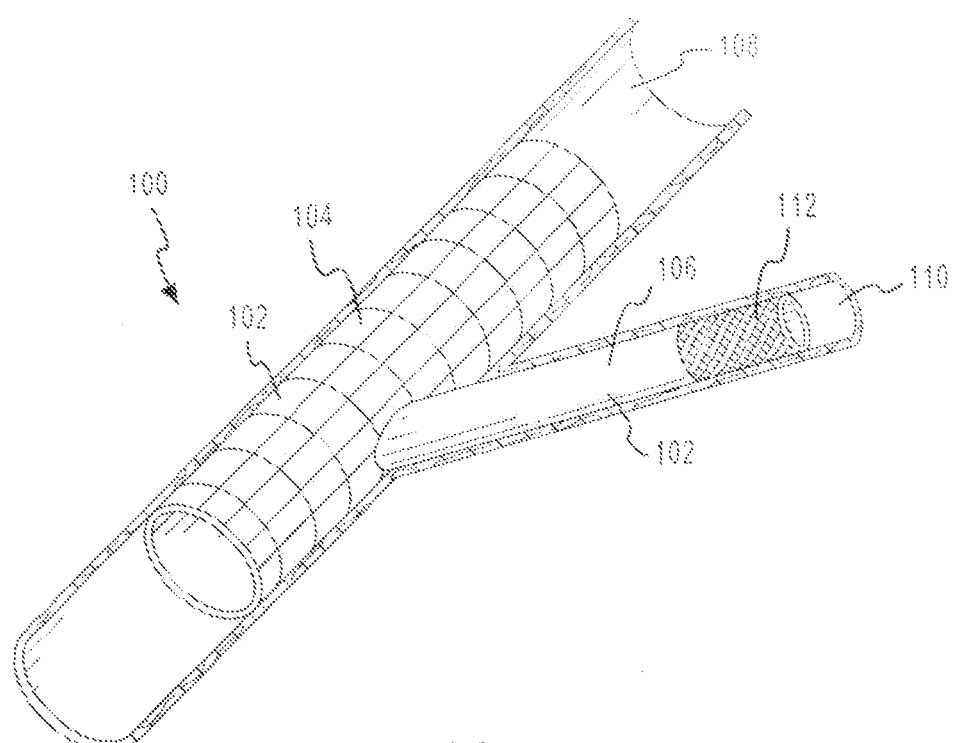
FIG. 1 is a perspective view of an exemplary embodiment of a prosthetic conduit with a side-branch shown within a cross-section of a vessel with a side-branch.

Referring to FIG. 1, a prosthetic conduit system 100 according to various aspects of the present invention includes a prosthetic conduit 102, such as a stent-graft. In various embodiments, the prosthetic conduit 102 includes a side-branch, and is suitable for placement in a main vessel 108 with a side-branch vessel 110. For example, the prosthetic conduit 102 may include a main member 104 and a side-branch member 106. Each of the main member 104 and the side-branch member 106 may include one or more stents and one or more sections of graft material.

Although the present exemplary embodiment comprises the stent-graft having one main member 104 with one side-branch member 106, the various configurations of a prosthetic conduit are not so limited, and may be configured in any suitable manner for the particular application and/or environment. For example, the main member 104 may have a bifurcation at one or both ends, two or more side-branch members 106 may be included, and the like. The prosthetic conduit 102 may include one continuous piece of graft material and multiple stents, one continuous stent-graft, or any suitable combination of one or more stents and/or one or more pieces of graft material. Furthermore, the side-branch member 106 may be configured to branch from the main member at any suitable angle. The side-branch member 106 may be further configured to adapt to a range of angles to allow for placement into multiple different configurations of main vessel 108 and side-branch vessel 110.

Similarly, the prosthetic conduit 102 may have any suitable size or combination of sizes. For example, the main member 104 may be configured for placement within a relatively large main vessel 108, such as the abdominal aorta, while side-branch member 106 may be configured for placement within a relatively small side-branch vessel 110, such as a renal artery. In another embodiment, both the main member 104 and side-branch member 106 may be relatively small, for example if the prosthetic conduit is configured to be placed in human coronary arteries. Thus, the prosthetic conduit 102, including the main member 104 and side-branch member 106, may have any suitable dimensions.

In a first exemplary embodiment, the entire length of the main member 104 comprises a combination of stent and graft material, while the side-branch member 106 includes a graft material along its entire length with a side-branch stent 112 located at its distal end. In another embodiment, each of the main member 104 and the side-branch member 106 comprises a single continuous piece of graft material and multiple stents. Alternatively, the prosthetic conduit 102 may comprise one continuous stent-graft comprised of a single graft and a single stent. Further, the prosthetic conduit 102 may comprise one or more grafts with no stents or one or more stents with no graft sections. Thus, the prosthetic conduit 102 may comprise various combinations of one or more stents and one or more pieces of graft material.

Figure 2:
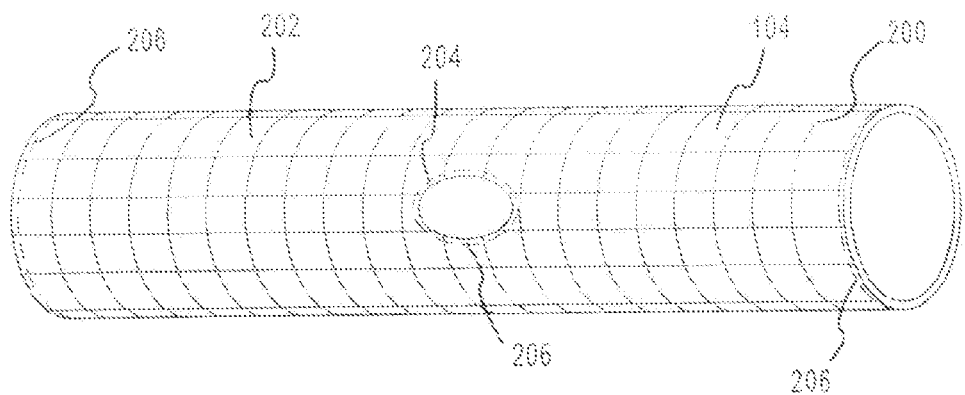
FIG. 2 is a perspective view of an exemplary embodiment of a main member of a prosthetic conduit.

Referring now to FIG. 2, the main member 104 may be configured to provide a main blood flow conduit and may include a support for the conduit to keep it open. Further, the main member 104 may be configured to provide flow to and/or from the side-branch member 106. In the present embodiment, the main member suitably has a generally tubular configuration with open ends, and comprises a main stent 200, a main graft 202, and at least one side opening 204. The main stent 200 provides support to maintain the desired position and/or configuration of the prosthetic conduit 102. The main stent 200 may be a single stent or a plurality of stents, and may be present along the entire length of the main member 104, or only in sections, and may extend beyond the length of the main graft 202. The main stent 200 may be incorporated into the main member 104 in any location by any suitable method, or may be installed separately. The main stent 200 may be deployed in any appropriate manner, such as balloon expansion, self-expansion, or any suitable combination of both, and may be constructed of a variety of materials or combinations, such as, but not limited to, metals or alloys (stainless steel, titanium, tantalum, nitinol and the like), polymers, carbon, ceramics and the like.

Alternative embodiments of the main member 104 may also include other or additional mechanisms for supporting and/or securing the main member 104 to a surrounding organism vessel 108. Stents or other suitable devices, for example, may be utilized to provide additional support and/or strength to the main member 104, such that the main stent 200 may be supplemented, replaced, or omitted altogether. Further, the main member 104 may be secured in position by an adhesive on at least a portion of the main member 104 outer surface (or the inner surface of the attachment site), a set of barbs or pins attached to the main member 104 and engaging the surrounding tissue, and the like.

The main graft 202 provides a conduit for fluid flow through the main member 104. The main graft 202 may be comprised of any suitable material, such as a biocompatible material, or combination of materials, such as, but not limited to, polyester, polyether sulfone, polyethylene, polytetrafluoroethylene (PTFE), polyurethane and the like. Further, the materials may be configured or treated in any manner to achieve selected characteristics. For example, the material may be treated in accordance with the disclosure of U.S. Pat. No. 5,800,522, issued Sep. 1, 1998, to Campbell, et al. Moreover, the main graft 202 may be comprised of various forms or combinations of forms, such as, but not limited to, extruded tubing, braided tubing, textile tubing, tubing created from the wrapping and bonding of thin films, and the like. The main graft 202 may be of any suitable porosity.

In the present embodiment, the main graft 202 includes a thin, flexible material, such as polyethylene. In the present embodiment, the main graft 202 is not treated, as described below, to be circumferentially distensible. The main graft 202 may, however, comprise any suitable material, including a material that may be distended with minimal foreshortening and recoil to conform to the organism vessel 108, 110, the stents 112, 200, or other characteristic. If the main graft 202 material is distensible (for example, as described and defined in U.S. Pat. No. 5,800,522, issued Sep. 1, 1998, to Campbell, et al.), the graft material may be circumferentially distended along its entire length, or in selected portions. Various coatings or treatments can be applied to either the main stent 200, the main graft 202, or both, to render the main member 104 more biocompatible (pyrolytic carbon, hydrogels and the like) and/or to provide for the elution of drugs (heparin, anti-platelet agents, platelet derived growth factors, antibiotics, steroids and the like). Additionally, various coatings or treatments may be applied to either the main stent 200, the main graft 202, or both, to render the main member 104 radioactive.

The main graft 202 may be configured to be placed on either the inner surface or the outer surface of the main stent 200, or in any suitable position relative to the inner or outer surface of the main stent 200. The main stent 200 and main graft 202 may be connected before placement into a vessel, or the main stent 200 and main graft 202 may be inserted into a vessel separately and connected within the vessel. In either case, the main graft 202 may be attached to the main stent 200 by any suitable mechanism. Certain embodiments of the main member 104 may be manufactured by a lamination process so that the material of the main graft 202 covers both the inner and outer surfaces of the main stent 200.

The main member 104 may include a radiopaque material to enhance the visibility of the main member 104. For example, the main stent 200 or the main graft 202 may be wholly or partially comprised of radiopaque materials. Alternatively, radiopaque markers 206 may be incorporated into the main graft 202 or the main stent 200, either throughout the structure or at one or more locations.

Figure 3:
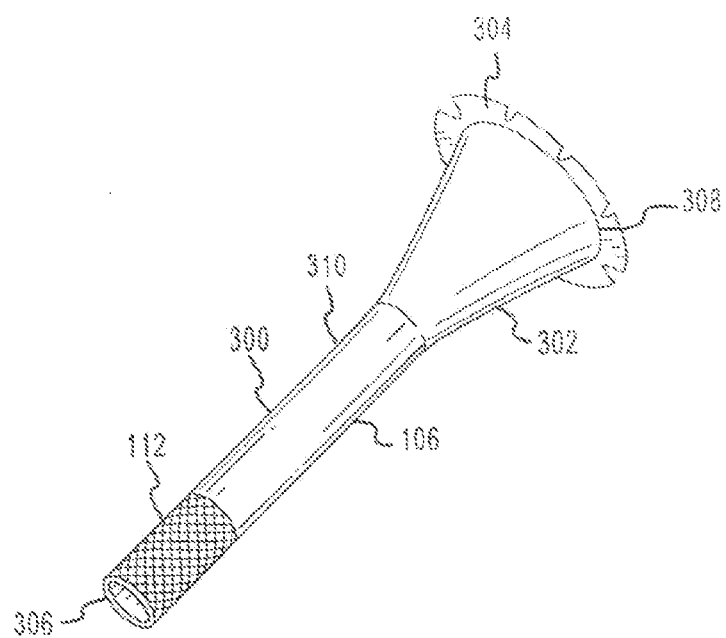
FIG. 3 is a perspective view of an exemplary embodiment of a side-branch member.

The side-branch member 106 facilitates flow between the main member 104 and a side-branch vessel 110. For example, referring to FIG. 3, the side-branch member 106 may have a generally tubular configuration with an open proximal end 308 and an open distal end 306. The side-branch member 106 suitably comprises a side-branch graft 310 for facilitating fluid flow between the main member 104 and the open distal end 306. The side-branch member 106 may also include a side-branch stent 112, for example to support the distal end 306. In the present exemplary embodiment, the side-branch member 106 includes a straight section 300, a conical section 302, and an attachment area, such as a flange 304.

Similar to the main member 104, the side-branch member 106 may suitably comprise a combination of one or more stents, such as the side-branch stent 112, and one or more sections of graft material, such as the side-branch graft 310. The side-branch member 106 may include any suitable combination of stents (if desired) and graft material. For example, one or more stents may be used in one side-branch member 106, and/or stents may be placed entirely within the length of the side-branch graft 310 or may extend beyond the length of the side-branch graft 310, protruding further into the side-branch vessel 110.

The side-branch stent retains the side-branch graft 310 in an open position and/or secures the position of the side-branch graft 310. The side-branch stent 112 may be positioned in any suitable manner, such as by placing the stent in a desired position and expanding the stent within the organism vessel 110. The side-branch stent 112 may be balloon expandable, self-expanding, or any combination, and may be constructed from one or more of a variety of suitable materials, such as, but not limited to, metal or alloys (stainless steel, titanium, tantalum, nitinol and the like), polymers possessing varying degrees of bioabsorbtion and biodegradation, carbon, ceramics, and the like.

The side-branch stent 112 may be configured such that it is in contact with the inner or outer surface of the side-branch graft 310 or a combination of both. The side-branch stent 112 may engage or be attached to the side-branch graft 310 in any appropriate manner. For example, in one embodiment, the side-branch stent 112 may be inserted into a vessel as a separate piece and may be attached to the side-branch graft 310 within the side-branch vessel 110. In other embodiments, the side-branch stent 112 is configured to be implanted at the same time as the side-branch graft 310.

The side-branch graft 310 may be constructed from one or more of a variety of suitable materials, such as, but not limited to, polyester, polyether sulfone, polyethylene, polytetrafluoroethylene, polyurethane and the like. The side-branch graft 310 may be of any suitable porosity. In the present embodiment, the side-branch graft 310 includes a thin, strong, flexible, and/or kink resistant material. For example, the side-branch graft 310 suitably includes a material, such as treated polyethylene, that may be circumferentially distended without significant foreshortening and/or recoil. The graft material may be circumferentially distensible along its entire length, or in selected portions. Further, the materials may be configured or treated in any manner to achieve selected characteristics. For example, the material may be treated in accordance with the disclosure of U.S. Pat. No. 5,800,522, issued Sep. 1, 1998, to Campbell, et al. Furthermore, side-branch graft 310 may be comprised of various forms or combinations of forms, such as, but not limited to, extruded tubing, braided tubing, textile tubing, tubing created from the wrapping and bonding of thin films, and the like.

Various coatings or treatments may be applied to render the side-branch stent 112 and/or the side-branch graft 310 more biocompatible (pyrolytic carbon, hydrogels and the like) and to provide for the elution of drugs (heparin, anti-platelet agents, platelet derived growth factors, antibiotics, steroids and the like). Various coatings or treatments may be applied to render the side-branch stent 112 and/or the side-branch graft 310 radioactive. Further, the side-branch member 106 may include one or more areas, such as portions of the graft 310 and/or the side-branch stent 112, that are radiopaque. For example, the side-branch stent 112 may be constructed from one or more radiopaque materials and/or one or more radiopaque markers (not shown) may be placed on the graft 310 or the side-branch stent 112 materials at one or more locations along the side-branch member 106.

The side-branch member 106 is connected to the main member 104 to allow fluid flow between the two components. The side-branch member 106 is suitably connected via its proximal end 308 to the side opening 204 of the main member 104. In the present embodiment, the conical section 302 has a diameter that is larger at the proximal end 308 and tapers as it approaches the straight section 300. The proximal end 308 may be configured to fit within, around, or in any other suitable configuration with the side opening 204 of the main member 104.

The proximal end 308 may further include a mechanism, such as the attachment area including the flange 304, for facilitating attachment of the side-branch member 106 to the side opening 204 of the main member 104. The flange 304 may be bonded in any appropriate manner to the outer surface, the inner surface, or any other appropriate portion of the main member 104. The flange 304 may be incorporated into the proximal end 308 to provide a surface that may be easily positioned against and bonded to the perimeter of the side opening 204, for example to effect a liquid-tight and strong connection.

The side-branch member 106 may be configured for attachment to the main member 104 at any suitable angle. The prosthetic conduit 102 may be provided in multiple angular and structural combinations, enabling a variety of configurations. Furthermore, the side-branch member 106, or a portion thereof, may be configured to allow flexibility, such that prosthetic conduit 102 may be used in a variety of different angles between the main vessel 108 and the side-branch vessel 110. For example, in one embodiment, a particular prosthetic conduit 102 may be placed or used in vessels having anywhere from a 25-degree angle to a 45-degree angle. Other embodiments may accommodate other angles and/or greater or lesser ranges of angles.

The prosthetic conduit system 100 according to various aspects of the present invention may be placed directly at a selected site. Alternatively, the prosthetic conduit system 100 may be introduced at a first site and delivered to the desired location using a delivery system. The prosthetic conduit system 100 may also include a deployment system for deploying the prosthetic conduit 102 at the selected site. The delivery system and/or the deployment system may be integrated into or independent from the prosthetic conduit 102. The delivery system suitably places and stabilizes the prosthetic conduit 102 at a desired location. The deployment system suitably configures and secures the prosthetic conduit 102 for operation following delivery.

Figure 4:
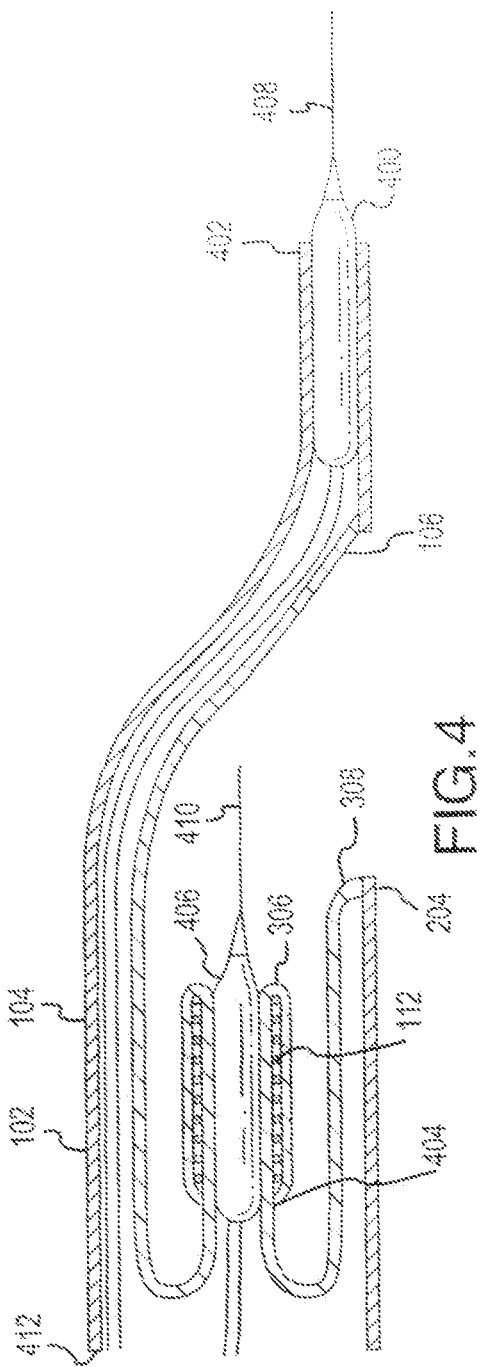
FIG. 4 is a cross-sectional view of an exemplary embodiment of a prosthetic conduit, shown with an apparatus for delivery, including a main guidewire, a main balloon catheter, a side-branch guidewire and a side-branch balloon catheter.

The delivery system for positioning the prosthetic conduit 102 in the desired position may comprise any suitable delivery system, such as, but not limited to, one or more balloon catheters, guidewires, introducer sheaths, guiding catheters, push tubes, and/or constraining sheaths. Referring to FIG. 4, an exemplary integrated delivery and deployment system according to various aspects of the present invention comprises a main guidewire 408, a main balloon catheter 400, a side-branch guidewire 410, and a side-branch balloon catheter 406. The main guidewire 408 and the side-branch guidewire 410 may comprise any suitable guides to facilitate navigation of the prosthetic conduit 102 to a desired location and extension of the side-branch member 106. The guidewires 408, 410 are advanced through the organism vessels to guide the prosthetic conduit 102 to the desired location.

The balloon catheters 400, 406 move the prosthetic conduit 102, secure the prosthetic conduit 102 in position, and/or deploy the prosthetic conduit 102. The main balloon catheter 400 and side-branch balloon catheter 406 may be conventional balloon catheters, and may possess varying degrees of compliance. For example, in some embodiments the balloon catheters 400, 406 may be highly compliant, such as embolectomy balloon catheters, while in other embodiments the balloon catheters 400, 406 may be non-compliant or semi-compliant high-pressure balloon dilation catheters. Additionally, the balloon catheters 400, 406 may be either over-the-wire or rapid-exchange balloon catheters.

The balloon catheters 400, 406 are configured to engage the guidewires 408, 410 so that the balloon catheters 400, 406 may move along the guidewires. The balloon catheters 400, 406 are also configured to engage the prosthetic conduit 102 to facilitate movement and deployment of the prosthetic conduit 102. For example, in the present embodiment, the distal end 402 of the main member 104 may be releasably attached, by any suitable mechanism, to the main balloon catheter 400, and the distal end 306 of the side-branch member 106 may be releasably attached to the side-branch balloon catheter 406.

The prosthetic conduit 102 may be equipped with the delivery system and/or deployment system prior to implantation. Alternatively, the delivery system may be provided at the time of implantation. For example, the main balloon catheter 400 may be integrated into the prosthetic conduit 102 at the time of manufacture, or may be connected to the prosthetic conduit 102 at the time of implantation. Similarly, the side-branch balloon catheter 406 may be omitted during the initial introduction of the prosthetic conduit 102 into the vasculature. The relatively small profile of the side-branch guidewire 410 may be advantageous in certain situations compared to the side-branch balloon catheter 406 or a tube. Thus, installation techniques and conduits may be selected according to the particular configuration, application, or situation.

Figure 5:
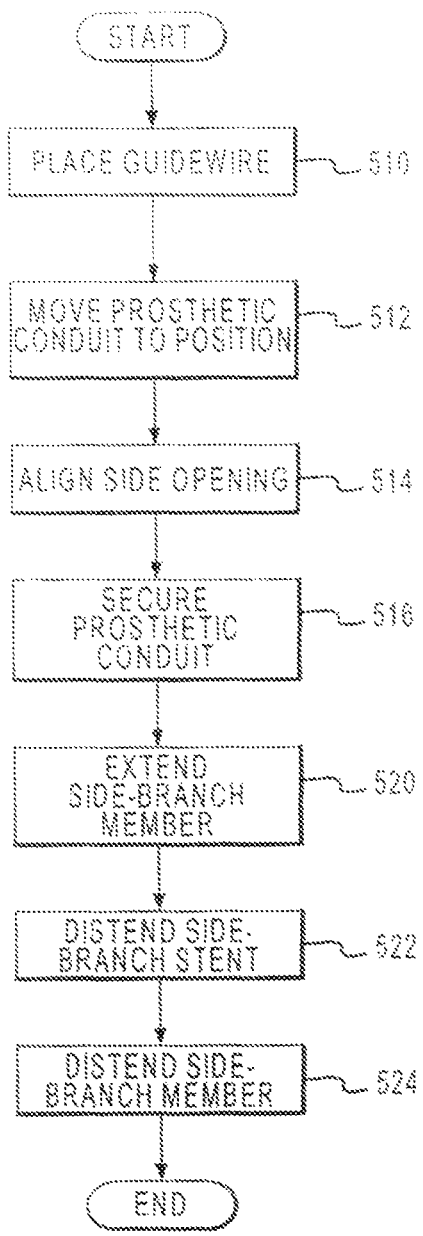
FIG. 5 is a flow chart illustrating an exemplary delivery and deployment process.

Referring to FIG. 5, to place the prosthetic conduit 102 at a desired location, the main guidewire 408 may be introduced into the vasculature and navigated into the main vessel 108 (step 510). The main balloon catheter 400, releasably attached to the distal end 402 of the main member, may be advanced along the main guidewire 408, advancing with it the prosthetic conduit 102 (step 512). To enhance accuracy of placement of the prosthetic conduit 102, the side-branch guidewire 410 may be used to align the side opening 204 of the main member 104 with the origin of the side-branch vessel 110 (step 514).

Figure 6:
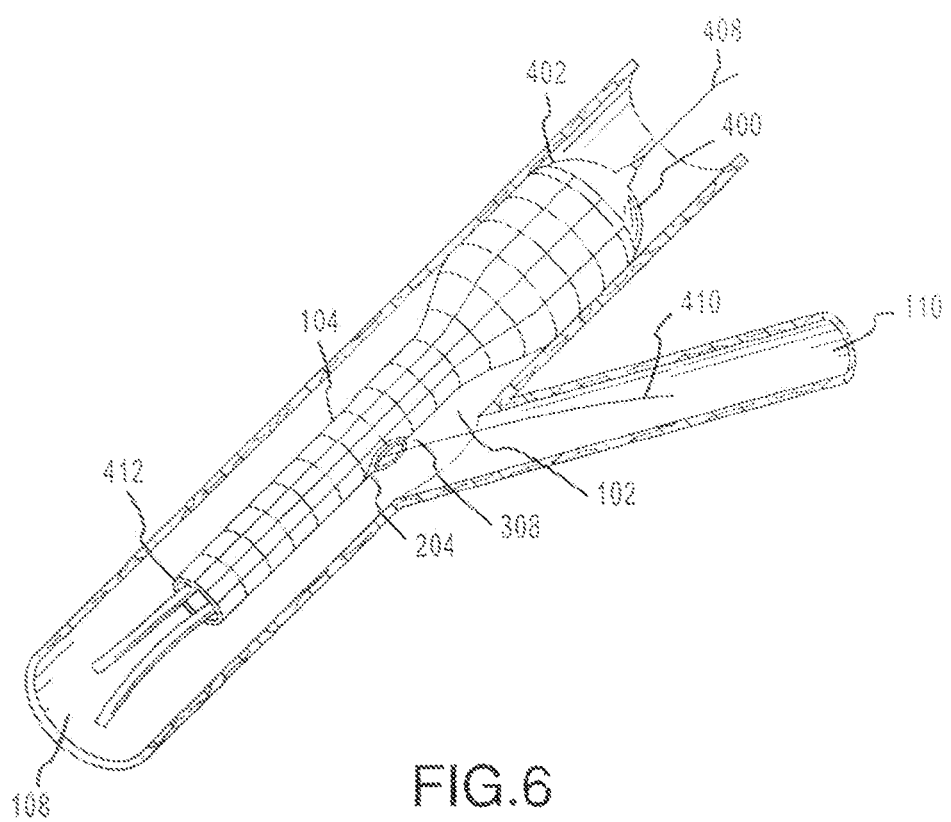
FIG. 6 is a perspective view of an exemplary embodiment of a prosthetic conduit, with the distal end of the main member inflated by a balloon catheter and the side-branch retracted, shown within a cross-section of a vessel with a side-branch.

When the prosthetic conduit 102 is placed at a desired location, it may be secured in the desired position (step 516), for example using the balloon catheters 400, 406. For example, referring to FIG. 6, upon properly positioning the prosthetic conduit 102, the main member distal end 402 may be secured in position, for example by inflating the main balloon catheter 400 while the side-branch member 106 remains retracted. The main member distal end 402 may be expanded by the main balloon catheter 400 until the distal end 402 contacts the inner surface of main vessel 108. Expansion of the main member distal end 402 tends to stabilize the prosthetic conduit 102 so that the side-branch member 106 may be extended from the main member 104 and into the side-branch vessel 110. The remainder of the main member 104 may also be fully expanded along its entire length, either by one or more balloon catheters, by self-expansion, or by other suitable methods or apparatus.

After the position of the prosthetic conduit 102 has been secured, it may be deployed for operation. Any suitable deployment system may be employed to deploy the prosthetic conduit 102, and the deployment system may be configured in any suitable manner to configure the prosthetic conduit 102 for operation. The prosthetic conduit 102 may be equipped with the deployment system prior to implantation or at the time of implantation.

In the present embodiment, the prosthetic conduit 102 is configured so that the side-branch member 106 is initially located within the main member 104 for delivery into a vessel. Such a configuration may ease delivery of the prosthetic conduit 102 into one or more vessels. Thus, the deployment system is suitably configured to extend the side-branch member 106 from within the main member 104 and into the side-branch vessel 110, and expand the main member 104 and side-branch member 106 to facilitate fluid flow. In particular, the deployment system includes the main guidewire 408, the side-branch guidewire 410, the main balloon catheter 400, and the side-branch balloon catheter 406. When the prosthetic conduit 102 is properly positioned within the vasculature by the delivery system, the side-branch balloon catheter 406 may be moved along the side-branch guidewire 410 to the distal end 306 of side-branch member 106, unless the side-branch balloon catheter 406 was placed simultaneously with the prosthetic conduit 102. The side-branch member 106 may be deployed by releasably attaching the side-branch balloon catheter 406 to the side-branch member 106 to extend the side-branch member 106 into the side-branch vessel 110. The side-branch member 106 is then suitably extended along the side-branch guidewire 410 and secured using the side-branch balloon catheter 406.

The side-branch balloon catheter 406 may be attached to the side-branch member 106 in any suitable manner, such as by crimping side-branch stent 112 and the surrounding graft material onto side-branch balloon catheter 406 to releasably attach side-branch balloon catheter 406 to the side-branch member 106. In the present embodiment, the side-branch balloon catheter 406 may be positioned within the side-branch stent 112 and inflated to a pressure high enough to engage the side-branch stent 112, but low enough to avoid substantial expansion of the side-branch stent 112.

Figure 7:
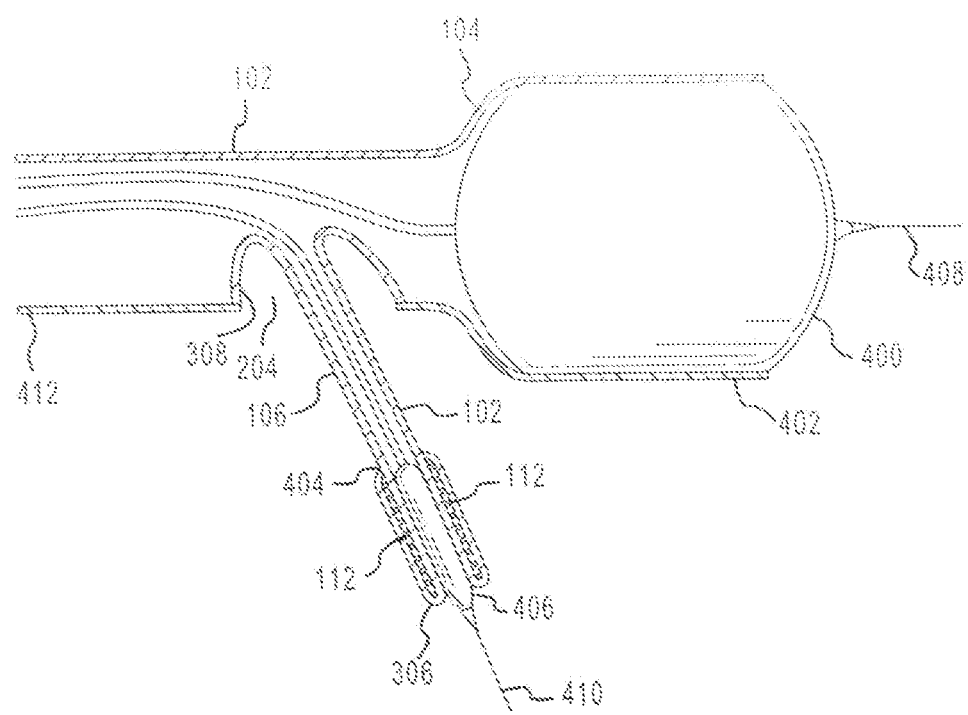
FIG. 7 is a cross-sectional view of an exemplary embodiment of a prosthetic conduit, with the distal end of the main member inflated with a balloon catheter and the side-branch member partially pushed out from within the main member.

Referring to FIG. 7, after releasably attaching the distal end 306 of the side-branch member 106 to the side-branch balloon catheter 406, the side-branch balloon catheter 406 and the side-branch member 106 may be advanced along the side-branch guidewire 410 to a desired location, thus extending the side-branch member 106 into the side-branch vessel 110 (step 520). After extending the side-branch member 106, the side-branch stent 112 is in a position to be expanded to secure the side-branch member 106 in position and facilitate flow. In an alternative embodiment, the side-branch stent 112 may be installed separately, after the side-branch member 106 has been otherwise pushed or pulled from inside the main member 104.

Figure 8:
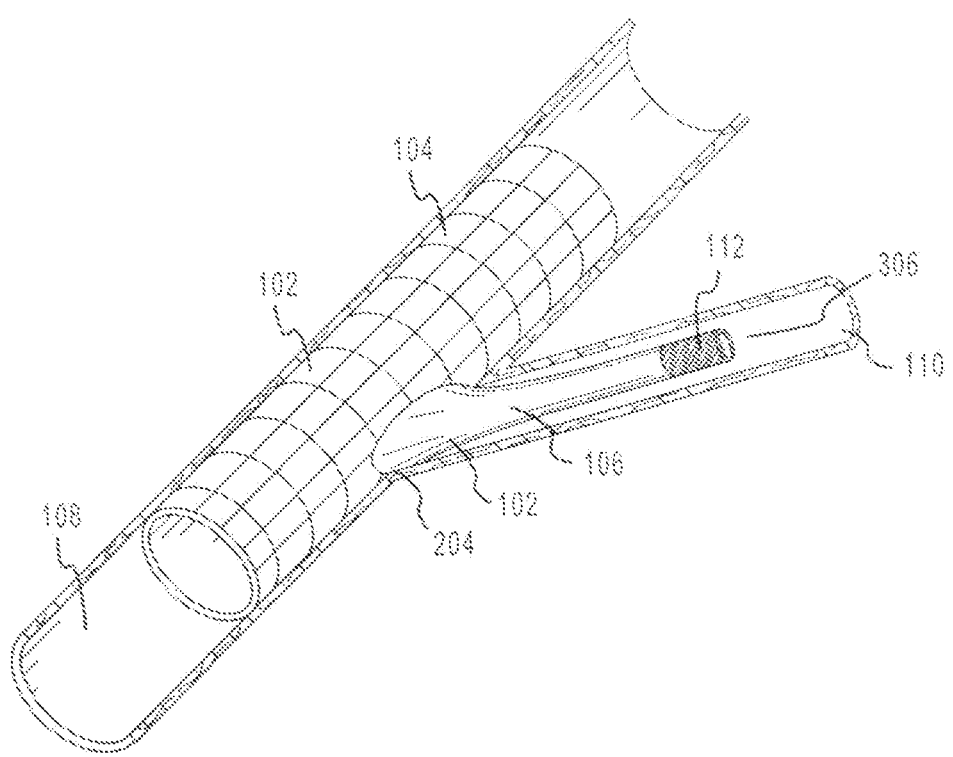
FIG. 8 is a perspective view of an exemplary embodiment of a prosthetic conduit, shown within a cross-section of a vessel with a side-branch, with the main member fully expanded and the side-branch member not fully expanded.

Referring to FIG. 8, the side-branch stent 112 may then be expanded to contact or adhere to the inner surface of the side-branch vessel 110 (step 522). For example, the side-branch balloon catheter 406 is inflated to a selected pressure and for a selected duration, causing the distal end of side-branch member 106 encompassing side-branch stent 112 to circumferentially distend. The pressure is then suitably released and side-branch balloon catheter 406 may be moved toward the proximal end of the side-branch member 106. The side-branch balloon 406 is inflated again, causing the adjacent region of the side-branch member 106 to distend. This process of circumferential distention may be repeated until the side-branch balloon catheter 406 distends the entire length of the side-branch member 106 (step 524). When the main member 104 is placed and fully dilated and the side-branch member 106 is fully extended and distended, the prosthetic conduit 102 is fully deployed and operational.

Figure 9:
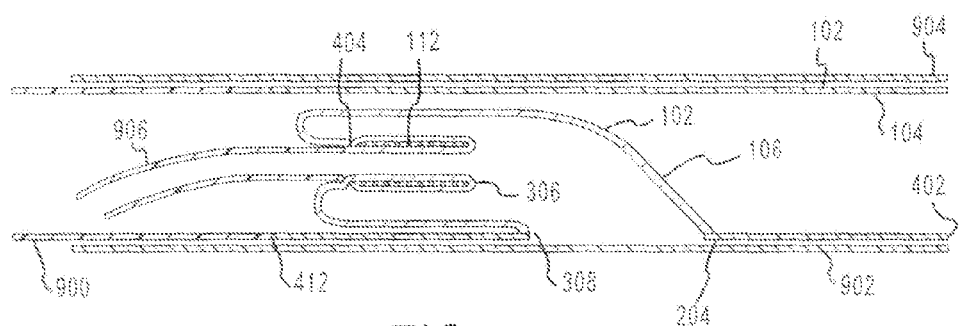
FIG. 9 is a cross-sectional view of an exemplary embodiment of a prosthetic conduit with a deployment tube.

The balloon catheters 400, 406 facilitate delivery of the prosthetic conduit 102 and extension of the side-branch member. Any suitable system, however, may be used to deliver and deploy the prosthetic conduit 102 and side-branch member 106. For example, a snare may be used to grasp the distal end 306 of side-branch member 106 and unfold it, either by pushing or pulling. Alternatively, referring to FIG. 9, the deployment system may include a deployment tube 906, which may be similar in outer diameter to the side-branch balloon 406 and positioned to provide a passageway into the distal end 306 of side-branch member 106. The lumen of the deployment tube 906 may accommodate other deployment elements for deploying the prosthetic conduit 102, such as guidewires, balloon devices, snares, or other selected devices or materials. The deployment tube 906 may comprise, for example, a guiding catheter and may have specific bends incorporated into its distal end to facilitate the deployment of the side-branch member 106. Any suitable embodiment of a deployment tube may be utilized. During installation, once the side-branch balloon catheter 406 is inserted into the distal end 306 of side-branch member 106, the deployment tube 906 may be removed or may be used as a support to stiffen and/or guide the side-branch balloon catheter 406, thus aiding in the deployment of the side-branch member 106. Thus, installation techniques and devices may be selected according to the particular configuration, application, or situation.

Figure 10:
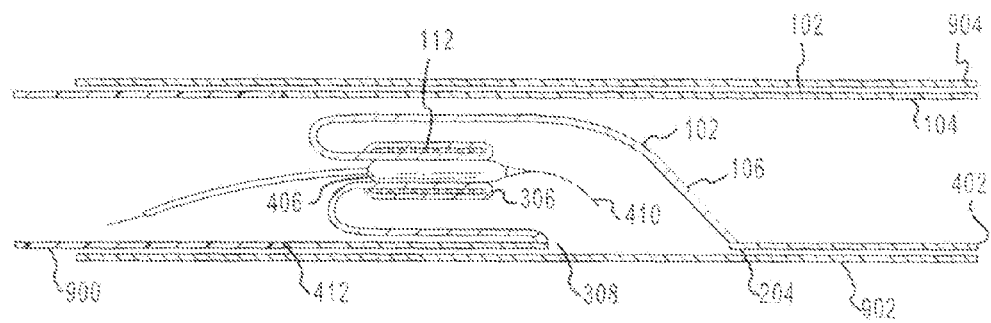
FIG. 10 is a cross-sectional view of an exemplary embodiment of a prosthetic conduit wherein the main member is self-expanding, shown with an apparatus for delivery including a constraining sheath, a push tube, a side-branch balloon catheter, and a side-branch guidewire.

Another embodiment of a delivery and deployment system according to various aspects of the present may be adapted to function with one or more self-expanding stents. For example, referring to FIGS. 9 and 10, the delivery system may include a push tube 900 and a constraining sheath 902 configured for maintaining the prosthetic conduit 102 in a compact configuration until delivery and deployment and delivering the prosthetic conduit 102 into the main vessel 108. Any suitable embodiment of a constraining sheath or structure to maintain the prosthetic conduit 102 in a compact configuration may be utilized.

The prosthetic conduit 102 and push tube 900 may be positioned within the constraining sheath 902 such that the proximal end 412 of the main member 104 is in contact with the distal end of the push tube 900. The constraining sheath 902 suitably contains the prosthetic conduit 102 and the push tube 900, and may be introduced into a vessel or other bodily conduit, for example as a catheter may be introduced, and may be advanced to a desired position within a vessel. When the prosthetic conduit 102 is advanced to a desired location, the constraining sheath 902 may be pulled back proximally, the push tube 900 may be pushed distally, or both, to release the prosthetic conduit 102 from the constraining sheath 902. Because the main member 104 may be self-expanding, once released from constraining sheath 902, the main member 104 may expand to contact the inner wall of main organism vessel 108.

The constraining sheath 902 may suitably include an aperture for allowing the side-branch guidewire 410 to protrude through the constraining sheath 902, which allows the side-branch guidewire 410 to help align the side opening 204 with the origin of the side-branch vessel 110. The side-branch guidewire 410 may be extended laterally from the constraining sheath 902 and into the side-branch vessel 110 to facilitate the correct positioning of the prosthetic conduit 102. When the prosthetic conduit 102 is correctly positioned, the side-branch guidewire 410 may be retracted, allowing the constraining sheath 902 to be moved axially with respect to the prosthetic conduit 102.

Figure 11:
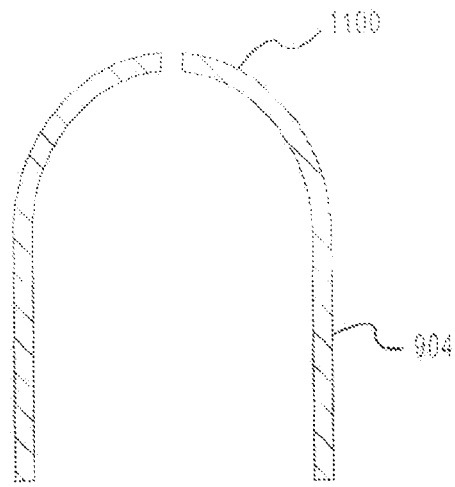
FIG. 11 is a cross-sectional view of an exemplary embodiment of the distal end of a constraining sheath configured to deliver a prosthetic conduit with a self-expanding main member within a vessel.
Figure 12:
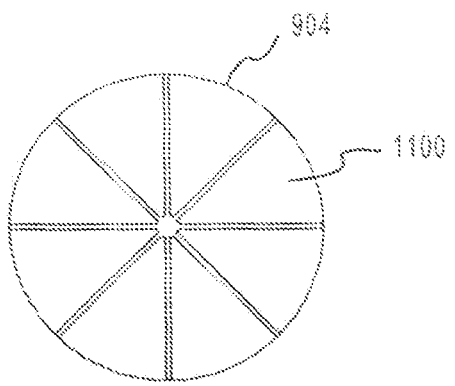
FIG. 12 is an end-on view of the distal end of an exemplary embodiment of the constraining sheath used to deliver a prosthetic conduit with a self-expanding main member within a vessel.

The constraining sheath 902 may be configured to the particular application and environment. For example, referring to FIGS. 11 and 12, the constraining sheath 902 may include a distal tip 904, configured to enhance navigability of the constraining sheath 902 within bodily conduits. The distal tip 904 may be configured to have a tapered profile that reduces resistance during movement within bodily conduits and may suitably include multiple wedge-shaped segments 1100. The tapered profile and wedge-shaped segments 1100 may enhance navigability within bodily conduits by providing a more hydro-dynamic distal tip 904 for the constraining sheath 902. The distal tip 904 may also be configured as a substantially closed structure to inhibit bodily fluids from entering the constraining sheath 902. Furthermore, the wedge-shaped segments 1100 may be configured to be flexible, allowing the constraining sheath 902 to be easily moved relative to the prosthetic conduit 102.

Figure 13:
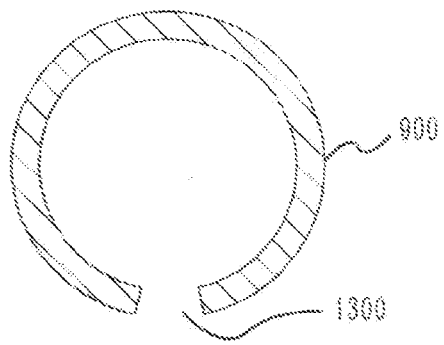
FIG. 13 is a cross-sectional, end-on view of an exemplary embodiment of a push tube device configured to deliver a prosthetic conduit with a self-expanding main member within a vessel.

The push tube may be configured in any suitable manner to facilitate delivery of the prosthetic conduit 102. For example, referring to FIG. 13, an exemplary embodiment of a push tube 900 configured to deliver the prosthetic conduit 102 with the self-expanding main member 104 within an organism vessel may include a cross-section shaped as an incomplete annulus with a gap 1300. The push tube 900 with the gap 1300 may be configured to enable the push tube 900 to be easily removed from the organism vessel after deployment of the prosthetic conduit 102 without removing or otherwise disturbing the side-branch balloon catheter 406 or the side-branch guidewire 410.

The push tube 900 may also include a section that extends within the lumen of the main member 104, providing additional stiffness during installation. The push tube 900 may also include a section extending along the entire length of the main member 104, and abutting the distal end 402 of the main member 104, which tends to offer further control during installation of the prosthetic conduit 102.

The side-branch member 106 may be pushed or pulled out of the interior of the main member 104 in any suitable manner, for example by pushing it out with the releasably attachable side-branch balloon catheter 406. Thus, in this embodiment, the main member 104 is self-expanding while the side-branch member 106 is balloon expandable. Any suitable deployment system, however, may be used to extend the side-branch member 106 from within the main member 104.

The prosthetic conduit 102 according to various aspects of the present invention may be manufactured from many different materials or combinations of materials and may be constructed by any suitable method. A prosthetic conduit 102 according to various aspects of the present invention, however, is formed using material that may be circumferentially distended with minimal foreshortening and recoil. Accordingly, the material(s) for the prosthetic conduit 102 may be treated to facilitate such distention characteristics.

For example, referring to FIG. 14A-B, the main member 104 may be constructed by initially forming a film-tube (step 1410) of a thin, flexible material, such as a microporous polyethylene film, for example a segment of Solupor® 7P03A microporous polyethylene film manufactured by DSM Solutech. In the present embodiment, the film has a nominal thickness of about 50μ, a nominal porosity of about 85%, and a nominal weight per surface area of 7 g/m2, though any of these characteristics may vary according to the particular application. Various alternative film-tubes may be employed. For example, films of any suitable material, both porous and non-porous may be used. The diameter and wall thickness of the graft component of main member 104 may be constant or may vary to create graft components with different properties and different geometries, such as but not limited to tapers and the like.

To form the main film-tube, the film is cut to a selected size, such as an approximately 230×155 mm rectangular piece, and wrapped around the circumference of a mandrel, suitably comprising stainless steel, and having a desired diameter, such as about 16 mm, to form a film-tube. Various tooling (mandrels, rods, etc) may be used. The tooling onto which the film is applied may be of a constant outer diameter, or may have a variable outer diameter to create tubes of various geometries such as tapers and the like. Any suitable tooling having any suitable shape may be employed.

In the present embodiment, the tube is wrapped in a direction perpendicular to the major axis of the tube. The film may be wrapped in any suitable manner, for example, helically with respect to the major axis of the tube, or in any other appropriate manner. The wrapping is completed with the 230 mm long edges of the rectangular piece parallel to the major axis of the mandrel such that a desired thickness is achieved. In the present embodiment, approximately three layers of the film cover the mandrel. The circumference of the 16 mm mandrel is approximately 50.3 mm, so to achieve a film thickness of approximately three layers after wrapping, one side of the rectangular piece is cut to a dimension of about 155 mm, providing a selected overlap length, such as approximately 4 mm. During wrapping, the film may be treated, such as wet with isopropyl alcohol, to enable the film to better lay smoothly.

With the wrapping complete, both ends of the wrapped film section are secured to the mandrel, such as with wire. Next, the polyethylene film may be secured along its length to the mandrel. For example, the polyethylene section may be helically wrapped with porous polytetrafluoroethylene film, suitably covering the film-tube entirely, ensuring that the layers of the polyethylene film contact each other.

The layers of the wrapped film are bonded together to form a single tube (step 1412). Bonding of the layers may be achieved by any suitable method. For example, the 16 mm mandrel may be placed in an air convection oven set at 150° C. for 10 minutes and subsequently removed and allowed to cool. Once cool, the helically wrapped porous PTFE film as well as the securing wire are removed and discarded. The resulting 16 mm inner diameter polyethylene tube is then removed from the 16 mm outer diameter mandrel. The 150° C. temperature and 10 minute time combination is chosen to bond the film layers to each other, forming a robust tube, but leaving the porous nature of the polyethylene film substantially unchanged, and avoiding thermal degradation of the film. Any suitable temperature and time combination, however, may be used. Alternatively, heated dies that contact the film either partially or wholly may also be used. Further, various adhesives or coatings may be applied to the film to effect bonding. The use of such adhesives or coatings may result in tubes that are composite in nature, having the combined characteristics of the adhesive or coating as well as the characteristics of the film material.

In the present embodiment, the main member 104 is a polyethylene film-tube without any stent. Alternative embodiments of main member 104 may include stents of any suitable number, form, and material and may make use of various methods of attaching or incorporating the stents to the main graft 202.

In an alternative embodiment of main member 104, for example, a lamination process may be used to secure main graft 202 to main stent 200. In this exemplary embodiment the main graft 202 is made from Solupor® 8P07A microporous polyethylene film manufactured by DSM Solutech. The film has a nominal thickness of about 50μ, a nominal porosity of about 85%, and a nominal weight per surface area of 8 g/m2, though any of these characteristics may vary according to the particular application.

To form the main member 104, two rectangular pieces of the polyethylene film and a self-expanding stent are utilized. The two film pieces have respective dimensions of approximately 32×66 mm and 32×69 mm. A 9.25 mm stainless steel mandrel may serve as the form about which the pieces of film may be wrapped. Prior to applying the polyethylene film onto the mandrel, the mandrel is wrapped helically with porous PTFE film. The helical wrapping is done so as to create a uniform surface onto which the polyethylene film may be applied. This helical wrap serves as an underlayer over which the main member 104 is constructed. The 32×66 mm rectangular section of polyethylene film is next wrapped over the PTFE wrapped 9.25 mm mandrel. The wrapping is completed with the 32 mm long edges of the film section parallel to the major axis of the mandrel. As previously mentioned, during wrapping the polyethylene film may be treated, such as wet with isopropyl alcohol, enabling the film to lay more smoothly and form about the circumference of the PTFE wrapped mandrel more easily.

With the 32×66 mm section of polyethylene film wrapped about the PTFE wrapped mandrel, the self-expanding stent is carefully slid coaxially over the polyethylene film section. The self-expanding stent has a nominal inner diameter of 10 mm and a length of approximately 42 mm. The stent is centered along its length with respect to the section of the polyethylene film. This results in the stent extending approximately 5 mm beyond either edge of the polyethylene film section. The self-expanding stent utilized in this alternative embodiment of the main member 104 consists of 9 connected "Z" rings, with the outermost ring at each end flared to a larger diameter. The 5 mm lengths of stent extending beyond the edges of the polyethylene film section correspond to the two flared outermost "Z" rings.

With the self-expanding stent carefully positioned over the 32×66 mm rectangular polyethylene film section, porous PTFE film is used to wrap the flared outermost "Z" rings of the stent and bring them into contact with the PTFE film wrapped mandrel. The 32×69 mm rectangular film section is next wrapped over the self-expanding stent. The wrapping is completed with the 32 mm long edges of the film section parallel to the major axis of the mandrel and aligned with the polyethylene film section underneath the self-expanding stent. Again, during wrapping the polyethylene film may be treated, such as wet with isopropyl alcohol, to enable the film to lay more smoothly and form about the circumference of the self-expanding stent more easily.

Next, the entire assembly of the 32×69 mm section of polyethylene film, the self-expanding stent and the 32×66 mm section of polyethylene film may be secured along its length to the porous PTFE wrapped mandrel. For example, the entire assembly may be helically wrapped with porous polytetrafluoroethylene film, ensuring that the layers of the polyethylene film and the self-expanding stent suitably contact each other.

The layers of the assembly are bonded together to form the alternative embodiment of the main member 104. Bonding of the layers may be achieved by any suitable method. For example, the 9.25 mm mandrel may be placed in an air convection oven set at 140° C. for 10 minutes and subsequently removed and allowed to cool. Once cool, the helically wrapped porous PTFE film on the outside of the assembly as well as the PTFE film constraining the outermost "Z" rings of the self-expanding stent is removed and discarded. Next, the porous PTFE film wrapped about the circumference of the 9.25 mm mandrel is removed by carefully pulling on the free end of the film and causing it to unwrap underneath the alternative embodiment of the main member 104. The resulting main member 104 is then removed from the 9.25 mm outer diameter mandrel.

In yet another alternative embodiment of the main member 104, a textile component may be combined with the polyethylene film by way of lamination. As in the preceding embodiment, for example, Solupor® 8P07A microporous polyethylene film manufactured by DSM Solutech may be utilized. The main characteristics of the 8P07A film are described above. Although the 8P07A film is chosen for this particular exemplary embodiment, any suitable film or membrane made of any suitable material with any number of suitable characteristics may be used.

The textile component is a tubular braid made from polyethylene terephthalate (PET) fibers. The braid is made from a total of 36 strands of multifilament PET yarn and is manufactured by Secant Medical, Perkasie, Pa. Eighteen of the 36 strands are 44 denier, while the remaining eighteen are 20 denier. The tubular braid has an inner diameter of about 5 mm and a braid angle of about 100 degrees. Although this particular tubular braid is chosen for this embodiment, any suitable tubular braid of any suitable material may be employed. Additionally, the textile component need not be tubular. The textile component may come in any form, for example, in the form of a sheet or otherwise flat material and may be suitably applied to create any desired geometry. Furthermore, the textile component need not be braided. The textile component may be manufactured by any number of means such as but not limited to weaving or knitting. In certain embodiments the textile component may comprise individual strands of fibers arranged in any suitable pattern.

To form the main member 104, two rectangular pieces of the polyethylene film and a 55 mm long length of the PET braid are used. The two film pieces have respective dimensions of approximately 35×60 mm and 38×60 mm. A 4.1 mm stainless steel mandrel may serve as the form about which the main member 104 may be constructed. As described in the previous embodiment, prior to applying the polyethylene film onto the mandrel, the mandrel is wrapped helically with porous PTFE film. The helical wrapping is done so as to create a uniform surface onto which the polyethylene film may be applied. This helical wrap serves as an underlayer over which the alternative embodiment of the main member 104 is constructed. The 35×60 mm rectangular section of polyethylene film is next wrapped over the PTFE wrapped 4.1 mm mandrel. The wrapping is completed with the 60 mm long edges of the film section parallel to the major axis of the mandrel. As previously mentioned, during wrapping, the polyethylene film may be treated, such as wet with isopropyl alcohol, enabling the film to lay more smoothly and form about the circumference of the PTFE wrapped mandrel more easily. Any suitable treatment may be used to facilitate the wrapping.

With the 35×60 mm section of polyethylene film wrapped about the PTFE wrapped mandrel, the PET braid is carefully slid coaxially over the polyethylene film section. The braid is positioned such that it covers approximately half of the length of the polyethylene film section.

With the PET braid carefully positioned over half of the 35×60 mm rectangular polyethylene film section, the 38×60 mm rectangular film section is next wrapped over the 35×60 mm film section and the overlying braid. The wrapping is completed with the 60 mm long edges of the film section parallel to the major axis of the mandrel and aligned over the 35×60 mm polyethylene film section. Again, during wrapping, the polyethylene film may be treated, such as wet with isopropyl alcohol, to enable the film to lay more smoothly and form about the circumference of the 35×60 mm film section and the overlying braid more easily.

Next, the entire assembly of the 35×60 mm section of polyethylene film, the PET braid and the 38×60 mm section of polyethylene film may be secured along its length to the porous PTFE wrapped mandrel. For example, the entire assembly may be helically wrapped with porous polytetrafluoroethylene film, ensuring that the layers of the polyethylene film and the self-expanding stent suitably contact each other.

The layers of the assembly are bonded together to form the alternative embodiment of the main member 104. Bonding of the layers may be achieved by any suitable method. For example, the 4.1 mm mandrel may be placed in an air convection oven set at 140° C. for 10 minutes and subsequently removed and allowed to cool. Once cool, the helically wrapped porous PTFE film on the outside of the assembly is removed and discarded. Next, the porous PTFE film wrapped about the circumference of the 4.1 mm mandrel is removed by carefully pulling on the free end of the film and causing it to unwrap underneath the alternative embodiment of the main member 104. The resulting main member 104 is then carefully removed from the 4.1 mm outer diameter mandrel.

For both of the alternative embodiments of the main member 104 above, the 140° C. and 10 minute temperature and time combination is chosen to bond the various material layers to each other, forming a robust structure, but leaving the porous nature of the polyethylene film substantially unchanged, and avoiding thermal degradation of the film and the other materials utilized. Any suitable temperature and time combination, however, may be used.

Additionally, for both of the alternative embodiments of the main member 104 above, the mandrel over which the embodiment is constructed is wrapped helically with porous PTFE tape. The PTFE tape facilitates the removal of the finished main member 104 embodiment from the mandrel without significant distortion or damage. This is of particular concern for embodiments which include delicate stent and/or textile components or components of a generally fragile nature. Any suitable method may be employed to ease the removal of the finished main member 104 from its tooling. Various tapes or substrates of any suitable material may be applied in any suitable fashion to the surface of the tooling. The surface of the tooling may be treated with various coatings. The tooling itself may be collapsible or deformable by various means.

The two exemplary embodiments described above illustrate how various combinations of graft materials and stents may be combined to create different embodiments of the main member 104 with different characteristics. The process of laminating various materials and/or components to form the main member 104 and more generally, grafts and/or stent-grafts, affords a relatively simple and effective means of manufacturing complex devices. The lamination technique may obviate many tedious and costly manufacturing methods, for example, the use of sutures or thread to attach stent components onto grafts.

Returning now to the present exemplary embodiment of the main member 104, the 16 mm film-tube may then be cut, if desired, to a particular length, such as approximately 70 mm. The side opening 204 may then be formed in the tube, such as by using a 4 mm diameter biopsy punch (step 1414). Any suitable geometry and tooling may be employed to create the side opening 204. Additionally, alternative embodiments of the side opening 204 may include sections of material protruding laterally from the main member 104, to which the side-branch member 106 may be attached. It should be noted that although the exemplary embodiments of main member 104 are not processed to provide characteristics such as enhanced flexibility, kink resistance and limited foreshortening, such processing may be included using the methods described herein or by any other suitable means.

The side-branch member 106, such as an approximately 4 mm inner diameter polyethylene film-tube, may be formed in the same manner as the approximately 16 mm inner diameter polyethylene film-tube described above (step 1416). In particular, a graft material, such as 7P03A microporous polyethylene film, is cut to a selected size and shape, such as an approximately 230×42 mm rectangle, and wrapped around the circumference of a mandrel having the desired outer diameter, such as about 4 mm. In this instance, the circumference of the 4 mm mandrel is approximately 12.6 mm, so to achieve a film thickness of three layers after wrapping, one side of the rectangular piece is cut to a dimension of 42 mm, providing approximately 4 mm extra film length for overlap. During wrapping, the film may be wet with isopropyl alcohol to facilitate smooth layers.

With the wrapping complete, both ends of the 230 mm long wrapped film section may be secured to the mandrel, for example with wire. Next, the film is secured in position, such as by helically wrapping a porous PTFE film over the 230 mm long wrapped film section, covering the section substantially entirely. The PTFE film tends to secure the polyethylene film about the mandrel so that the layers of the polyethylene film contact each other.

The layers of the side-branch tube are then suitably bonded together to form the side-branch tube (step 1418). For example, the 4 mm mandrel may be placed in an air convection oven set at 150° C. for 5 minutes and subsequently removed and allowed to cool. Once cool, the helically wrapped porous polytetrafluoroethylene film as well as the securing wire are suitably removed and discarded. The temperature and duration may be selected according to any suitable criteria to bond the film layers to each other and form a robust tube, but substantially maintaining the porous nature of the polyethylene film and avoiding any significant thermal degradation or weakening of the film. The resulting 4 mm inner diameter polyethylene tube is then removed from the 4 mm outer diameter mandrel and suitably cut to a desired size, such as into two equal lengths.

In accordance with various aspects of the present invention, the side-branch tube and/or the main member 104 may be treated in any suitable manner to provide selected characteristics, such as circumferential distention and/or extension capabilities. In the present embodiment, the side-branch tube is treated to facilitate distention of at least a portion of the side-branch tube with relatively low foreshortening and/or recoil. The side-branch tube is also treated to facilitate kink resistance.

For example, the side-branch tube may be processed with cycles of heat, stretching, and/or compressing. The side-branch tube may be heated and stretched to a desired length and/or diameter. In the present embodiment, the side-branch tube may be initially marked at a known interval (step 1420), such as two marks at a 70 mm interval centered along the length of the side-branch tube. The film-tube is then secured to a mechanism configured to stretch the side-branch tube. Any suitable stretching apparatus may be used, and may include any suitable mechanism for securing the tube, stretching the tube, heating the tube, measuring, and/or controlling the amount and rate of stretching. For example, a sliding mandrel mechanism may comprise two lengths of 3 mm outer diameter stainless steel tubing and a length of 1.6 mm outer diameter stainless steel rod. One end of the rod is bent and inserted into one of the 3 mm outer diameter tubing lengths such that it is substantially immobile. Both lengths of the 3 mm outer diameter tubing have a 360° groove cut into the wall approximately 3 mm away from one end. The film-tube is fitted coaxially over the 1.6 mm rod and attached to the 3 mm outer diameter tubing by manually tying a wire over the film-tube and into the groove at the end of the 3 mm outer diameter tubing. The other length of 3 mm outer diameter tubing is then fitted coaxially over the 1.6 mm rod and the same manual wire tying process is used to secure the other end of the film-tube to the 3 mm outer diameter tubing.

When the side-branch tube is secured to the sliding mandrel mechanism, the assembly is exposed to heat (step 1422), such as via an air convection oven set at a selected temperature, such as 150° C. The oven is configured with holes at each end so that the sliding mandrel mechanism and the attached film-tube can be inserted such that the film-tube is approximately centered within the oven chamber and each of the 3 mm outer diameter tubing lengths extend out of each end of the oven. The side-branch tube is heated for a selected duration, such as one minute, and then slowly stretched by manually pulling the ends of the 3 mm outer diameter tubing lengths extending out of each end of the oven (step 1424). The film-tube is stretched in this manner to a desired length and/or diameter. Other parameters, such as the tensile force experienced by the tube, or the outer diameter of the tube during stretching may also be monitored and/or controlled.

In the present embodiment, the side-branch tube is stretched until the marks are approximately 130 mm apart. The lengthening causes the film-tube to reduce in diameter such that it substantially contacts the 1.6 mm rod. Tension is maintained on the film-tube, now stretched and reduced in diameter, ensuring that no significant change in length occurs while the sliding mandrel mechanism is removed from the oven. The film-tube is next allowed to cool and subsequently removed from the sliding mandrel mechanism.

At this point, the side-branch tube may be circumferentially distended. The side-branch tube may be further processed, however, to achieve additional characteristics. For example, the side-branch tube may be distended to facilitate later distention with reduced force up to a selected limit. For example, the side-branch tube may be initially distended to a first selected diameter (step 1426), such as by manually fitting the tube over a tapered stainless steel mandrel having a 2 mm outer diameter section approximately 200 mm in length, and tapering up to an outer diameter of 3.8 mm over a length of approximately 40 mm. When fitted entirely over the 3.8 mm outer diameter section of the mandrel and pulled taut, a distance of approximately 81 mm separates the two pen marks on the film-tube. Next, the tube is removed from the 3.8 mm tapered mandrel, and then further distended over a 4 mm tapered mandrel (step 1428). When fitted entirely over the 4 mm outer diameter section of the mandrel and pulled taut, a distance of approximately 75 mm separates the two pen marks on the film-tube. In the present embodiment, the distention is completed in two steps to make the process easier, though the distention may be performed in greater or fewer steps.

Varying amounts of distention may be performed to achieve varying final distensibility characteristics. The film-tube may be distended anywhere from zero to near the circumference at which it breaks, and the distention may be accomplished in any number of steps. The distention of the exemplary film-tube is suitably performed at ambient temperature conditions. Various temperature conditions, however, may be employed during the distention. The use of elevated temperature may be required for film-tubes of different materials, or for film-tubes of greater thickness. Moreover, any suitable mechanism and method may be employed to complete the distention. For example, as an alternative to the use of tapered mandrels, a balloon or bladder may be utilized to pressurize the film-tube and cause distention.

The side-branch tube may be further processed, such as to add features like flexibility and/or kink resistance. In the present embodiment, the side-branch tube is processed for kink resistance by sequentially stretching the tube to achieve a desired diameter and compressing the side-branch tube to form small corrugations. The corrugations may be formed in any suitable manner, and facilitate bending of the side-branch member 106 without kinks.

For example, the side-branch tube may be initially stretched (step 1430) using any suitable mechanism, such as a linear slide with a manually driven lead screw. Each end of the side-branch tube is secured onto the linear slide mechanism, for example using clamps. Heated air, such as from a hair drying gun set on low, may be applied to warm the side-branch tube and soften the graft material. Turning a hand crank connected to a lead screw actuates the linear slide. The film-tube may thus be slowly stretched. Periodically, the stretching of the film-tube may be halted, allowing the stress within the tube to diminish, thereby avoiding breaking of the tube. The film-tube is stretched until a desired distance, such as approximately 144 mm, separates the two marks on the side-branch tube. The film-tube may also be stretched until a desired diameter is achieved. The side-branch tube may then be allowed to cool and/or relieve stress for a selected time and temperature, such as at least five minutes at ambient temperature. The tube is then removed from the linear slide mechanism. The processes of distending the tube and subsequently stretching it to reduce its diameter may be repeated any number of times if desired.

The side-branch tube may also be processed to provide other characteristics, such as resistance to kinking and/or foreshortening. For example, to add kink resistance and reduce foreshortening upon distention, the side-branch tube may be processed to form corrugations. For example, the side-branch tube may be fitted coaxially over a 1.2 mm diameter stainless steel rod and again marked for reference (step 1432). The marks are separated by a selected interval, such as 50 mm, and the marks may be centered along the length of the side-branch tube. The side-branch tube is also suitably constrained against the rod, for example using a thin, strong, porous PTFE film helically wrapped over the side-branch tube.

The overwrapped side-branch tube on the 1.2 mm diameter rod may then be compressed. To facilitate compression, the side-branch tube is suitably heated (step 1434), such as in an air convection oven set at a selected temperature and duration, such as 70° C. for at least about 10 minutes. The side-branch tube may then be removed from the oven and compressed longitudinally (step 1436), tending to cause a reduction in length. The PTFE film overwrap tends to inhibit formation of gross corrugations along the surface of the film-tube during compression. Any suitable method may be used to control the size of the corrugations formed along the surface of the film-tube. For example, the film-tube while on the 1.2 mm diameter rod may be placed within a tube having an inner diameter slightly larger than the outer diameter of the film-tube prior to being overwrapped, and may then be longitudinally compressed within the tube.

The film-tube is longitudinally compressed a desired amount, for example so that a distance of approximately 28.5 mm separates the two pen marks originally separated by a distance of 50 mm. The side-branch tube may then cool to ambient temperature, the polytetrafluoroethylene film overwrap is removed, and the film-tube is removed from the 1.2 mm diameter rod. The resulting 1.2 mm inner diameter polyethylene film-tube may then be gently pulled (step 1438) or otherwise smoothed to remove any inconsistently large corrugations, leaving a substantially uniform tube surface.

The longitudinal compression tends to impart corrugations along the surface of the film-tube or otherwise shorten the film-tube. In some materials, like polyethylene, the compression may cause the tube surface to exhibit small corrugations or wrinkles. For other materials, the compression may cause compression of the material itself, such that the material condenses without forming corrugations in the surface. The porosity of the material and the temperature may also affect the formation of corrugations or other shortening of the film-tube. The wrinkles or other compression serve to enhance the flexibility of the tube, tending to allow the tube to undergo substantial bending without kinking, and also serve to inhibit any change in length of the film-tube during distention. The processes for achieving the various characteristics, including kink resistance and minimized foreshortening, may be applied to other materials as well, such as material treated in accordance with the disclosure of U.S. Pat. No. 5,800,522, issued Sep. 1, 1998, to Campbell, et al. Moreover, other methods may be applied to form corrugations or compress the tube, such as tying thin wires spaced at regular intervals around the circumference of the film-tube while the tube is on the 1.2 mm diameter rod. With the wires in place, the tube may be longitudinally compressed. The presence of the wires during the compression results in the formation of wrinkles of a pre-determined size.

Any number of methods may be used to enhance flexibility, kink resistance and foreshortening. The methods may be chosen to suit particular embodiments of graft components, main members and side-branch members incorporating various combinations of graft materials and stents. Grafts incorporating certain combinations of materials or certain combinations of stents and grafts may not easily be compressed longitudinally as described above. In such instances, other forms of manipulation may be employed to impart improved flexibility. For example, enhanced flexibility may be achieved by radial compression such as by rolling between plates, rolling manually, and/or usage of radial compression devices such as those manufactured by Machine Solutions, Inc. located in Flagstaff, Ariz. For certain embodiments gentle bending may be an effective method of increasing flexibility.

Although the graft component 310 described above is circumferentially distensible with low recoil and foreshortening, the use of non-distensible tubes as the graft component is possible. The graft component, distensible or not, may be of any suitable material known in the prior art, or any suitable material that may become available in the future. Additionally, graft component 310, may be constructed from any suitable form or combination of forms such as but not limited to extruded tubing, braided tubing, textile tubing, and as discussed tubing created from films or membranes. The graft component may be processed by any suitable methods. The wall thickness of the graft component 310 of the side-branch member 106 may be constant or may vary to create graft components with different properties. For example a graft component may have a thinner wall at the distal end, and a thicker wall at the proximal end, or vice versa. The graft component may further have any suitable degree of porosity.

Further, all of the techniques and materials may be applied to other components of the prosthetic conduit 102, such as the main member 104, or other devices and materials.

In an alternative embodiment, a graft component may be created from a woven textile tube. Woven textile tubes, such as braided tubes formed generally of helically wound strands, may be constructed from various suitable materials, such as but not limited to polyester, polypropylene, and polytetrafluoroethylene. Braided tubes may exhibit distensible behavior. Typically, distention of braided tubes is accompanied by pronounced foreshortening. The relationship between the amount of distention and the amount of foreshortening can be varied according to the parameters utilized in the manufacture of the tube.

A braided tube according to various aspects of the present invention is circumferentially distensible. A braided tube may be initially elongated in the direction of the major axis until the ensuing reduction in diameter is complete. Next, the tube may be cut to a selected length and fitted coaxially over a rod or mandrel of appropriate outer diameter. The ends of the tube are then secured to the rod or mandrel using wire, and the elongated braided tube is then overwrapped with porous polytetrafluoroethylene film and longitudinally compressed. The tube, prior to or during the longitudinal compression, may be heated.

The porous polytetrafluoroethylene film tends to control the size of corrugations along the surface of the tube. Next, for example, the tube is suitably placed in an oven and heated. The time and temperature parameters are suitably chosen such that the tube, after removal from the mandrel, substantially maintains the longitudinally compressed length, but the strands that form the tube are not permanently bonded to each other. In this fashion, the tube may be distended, but having been longitudinally compressed, foreshortens minimally. The braided tube may be gently pulled to remove any inconsistently large corrugations that may have been formed during the longitudinal compression process.

Any suitable degree of longitudinal compression may be performed to the braided tube. For example, in one embodiment two marks separated by a known distance may be placed on the braided tube prior to the tube being elongated, and the marks may be returned to their original spacing during the longitudinal compression process. Any suitable method may be employed to maintain the tube in its longitudinally compressed state but still allow distention. For example, a mild adhesive may be applied to the surface of the tube either partially or wholly. Alternatively, heated dies that contact the surface of the tube either partially or wholly may be used.

In accordance with various aspects of the present invention, the side-branch tube may be equipped with a support (step 1440), such as the side-branch stent 112 at the distal end of the side-branch member 106. The stent may be added to the side-branch tube in any appropriate manner. For example, one end of the 1.2 mm inner diameter polyethylene graft component may be slightly flared, such as by using a pair of small hemostats. The graft component may then be fitted coaxially onto a 1.2 mm diameter stainless steel rod and constrained against the rod, for example using a helical overwrap of thin, strong, porous PTFE film. The overwrapping suitably begins on the rod adjacent to the non-flared end of the graft component and ends at the base of the small flare at the end of the graft. The flared end of the graft may then be everted, for example manually using small hemostats. The PTFE overwrap film may be removed as necessary as the graft is everted until an everted section of a desired length, such as approximately 22 mm long, is obtained.

The stent may then be placed within the folded over portion of the graft. For example, a 0.64 mm diameter wire is suitably pushed underneath the everted section of the graft component, slightly distending the everted section, creating a small annular space between the everted section and the underlying graft component. A selected stent, such as an 18 mm long balloon-expandable side-branch stent 112, is then placed within the annular space between the everted section and the underlying graft component, the end of the side-branch stent 112 abutting the fold at the end of the everted section of the graft component.

The approximately 4 mm long length of everted graft component extending beyond the stent is then suitably bonded to the underlying graft component, for example using a conventional soldering iron, to maintain the position of the side-branch stent 112. The bonding process suitably controls the application of heat to ensure that the graft component is not overly heated, substantially changing the graft properties, or damaged during the bonding process. At this point, the everted section of graft component over the side-branch stent 112 may be radially compressed, reducing the outer diameter of the end of the graft component encompassing the stent. The remaining PTFE overwrap film may be removed and the graft component and stent are suitably removed from the 1.2 mm diameter rod.

Alternative embodiments of the side-branch tube may omit the side-branch stent 112 or replace it, for example with another type of stent. For example, the side-branch stent 112 may be a self-expanding stent. A suitable self-expanding stent may be placed within the annular space created between the everted section and the underlying film-tube as described. In such an embodiment the self-expanding stent may be maintained in a compact configuration by the graft component covering it, and thus the combination of the self-expanding stent and the graft component is functionally balloon expandable. One or more stents may be used at any location along the graft component. In some embodiments the use of both balloon expandable and self-expanding stents may be preferred. Further, any suitable method may be employed to attach or incorporate stents to the graft component. For example stents may sutured to the graft component, or may be attached by an adhesive. In some embodiments it may be possible to bond the stent to the graft component using heat.

In an exemplary embodiment according to various aspects of the present invention, an attachment area for attaching the main member 104 to the side-branch member 106 is provided (step 1442). For example, the side-branch member 106 suitably includes the conical section 302 and/or the flange 304. The conical section 302 may be formed in or attached to the side-branch member 106 in any suitable manner. For example, the portion of the graft component from the bond site 404 to the proximal end 308 is initially distended by coaxially fitting it over a 2 mm diameter steel rod, suitably such that the graft component does not compress longitudinally and become grossly corrugated, or substantially elongate. Once distended, the graft component and incorporated stent are suitably removed from the 2 mm diameter rod. In the present embodiment, the length of the graft component from the bond site 404 to the proximal end 308 is approximately 50 mm.

To form the conical section 302 and flange 304, the graft component, starting at the proximal end 308, is distended in a conical configuration, such as by fitting it over a 4 mm tapered mandrel. The tapered mandrel increases from an outer diameter of approximately 1.3 mm to an outer diameter of 4 mm over a length of approximately 30 mm. In the present embodiment, the graft component is fitted over the 4 mm tapered mandrel such that the proximal end extends approximately 6 mm onto the 4 mm outer diameter section of the mandrel.

Thus, in this particular embodiment, distending the proximal end 308 over a tapered or conically shaped mandrel at ambient temperature forms the conical section 302 of the side-branch member. The conical section may have any suitable geometry, provided that the proximal end of the side-branch member is able to be attached to the side opening 204 of the main member 104. Additionally, the conical section may be formed by any suitable method at any suitable temperature, such as for example distention via a balloon, or the use of any other tube flaring equipment. The method and temperature employed are dependent on the embodiment of the graft component. In an alternative embodiment, the conical section may be a separate piece, attached to the side-branch member by any suitable method.

Similarly, the flange may be formed in or attached to the side-branch member 106 in any suitable manner. For example, while side-branch member 106 remains situated on the 4 mm tapered mandrel, four cuts may be made at the proximal end of the graft component, for example using a razor blade. The cuts are suitably substantially parallel to the major axis of the graft component, extending approximately 3 mm from the proximal end of the graft component at selected intervals, such as 0, 90, 180, and 270° around the circumference of the proximal end 308 of the graft component. The four 3 mm long cuts form four substantially equal sections around the circumference of the proximal end 308 of the graft component. The four sections may then be bent to a position extending laterally, perpendicular to the major axis of the graft component, to form the flange 304. With the embodiment of the conical section 302 formed via the 4 mm tapered mandrel, and the embodiment of the flange created by the four equal sections around the circumference of the proximal end of the graft component, the graft component may then be removed from the 4 mm tapered mandrel.

The flange 304 may be of any suitable geometry to facilitate and/or strengthen the connection of the side-branch member to the main member. The flange 304 may be formed by any suitable mechanism, such as, but not limited to, flaring the proximal end 308 of the side-branch member 106 and then everting the flared section, or using any other suitable tube flanging equipment or process. Alternatively, the flange 304 may be a separate piece, attached to the side-branch member 106 by any suitable method, or attached to the side opening 204, or formed from the material surrounding the side opening 204. Any adaptation of the proximal end 308 of the side-branch member 106, or the side opening 204 in the main member 104, either alone or in combination, may be utilized.

The main member 104 and side-branch member 106 may be connected according to any suitable technique or process (step 1444). In the present embodiment, for example, the main member 104 is partially fitted coaxially onto a 16 mm outer diameter mandrel, leaving the lumen of the main member 104 and the side opening 204 accessible. The side-branch member 106 may be inserted, distal end first, into the lumen of the main member 104 and through the side opening 204 until the flange 304 abuts the inner surface of side opening 204.

When the flange 304 abuts the inner surface of the main member at the side opening 204, the flange 304 may be secured to the main member 104 in any suitable manner. For example, the main member 104 may be advanced down the length of the 16 mm outer diameter mandrel, trapping the four equal sections comprising the flange 304 between the mandrel and the main member 104. The main member 104 and the side-branch member 106, via flange 304, are then bonded together, for example thermally, at the side opening 204, such as via a soldering iron. The bonding, however, may be performed using any suitable mechanism or techniques, such as, but not limited to, sutures or adhesives.

The prosthetic conduit 102 may be configured in any suitable manner for delivery. In the present embodiment, the side-branch member 106 and the main member 104 are connected and placed in a compact configuration for delivery, for example with the side-branch member 106 inside of the main member 104. A delivery and/or a deployment system, either wholly or in part, may also be added to the assembled prosthetic conduit 102.

The prosthetic conduit 102 may be configured for delivery and deployment in any appropriate manner. For example, the side-branch member 106 may be disposed inside the main member 104 to facilitate placement (step 1446). In the present embodiment, a 1.2 mm diameter stainless steel rod is inserted coaxially within the side-branch member 106. To enable eversion of the side-branch member 106, the side-branch member is suitably constrained from dilation or longitudinal compression, such as by helically overwrapping the side-branch member 106 to the rod using porous polytetrafluoroethylene film. The overwrap suitably begins on the 1.2 mm diameter rod adjacent to the distal end 306 of the side-branch member 106 and ends adjacent to the proximal end 308 of the side-branch member 106. In the present embodiment, since all regions of the side-branch member 106 with exception to the region encompassing side-branch stent 112 have an inner diameter larger than 1.2 mm, care is taken during the application of the overwrap film, creating lengthwise folds and avoiding twisting of the side-branch member 106. Alternatively, to enable folding, the side-branch member 106 may be covered with an elastomeric tube of appropriate inner diameter and thickness.

The 1.2 mm diameter rod is then suitably used to push the side-branch member 106 into the lumen of the main member 104, causing the side-branch member to evert onto itself until a desired portion, such as the entire length of side-branch member 106, resides within the lumen of the main member 104. During the eversion process, the porous polytetrafluoroethylene film may be removed as necessary. Alternatively, if an elastomeric tube is used, the tube may be of sufficient length to evert over itself, leaving a free end extending beyond the distal end of the side-branch member 106. During the eversion of the side-branch member 106 into the main member 104, the elastomeric tube could be removed via eversion in the opposite direction. Once the side-branch member 106 is completely everted, the remaining overwrap film and the 1.2 mm diameter rod may be removed.

In the illustrative embodiment, the side-branch balloon catheter 406 is positioned within the side-branch member after the eversion process is completed. In an alternative embodiment, a side-branch guidewire 410 may be positioned within the everted side-branch member 106. In such an embodiment, the side-branch balloon catheter 406 may or may not be included within the side-branch member 106.

In another alternative embodiment, the side-branch balloon catheter 406 may be placed coaxially within the side-branch member 106, in lieu of the 1.2 mm diameter rod. The side-branch balloon catheter 406 may be located at any suitable place along the length of the side-branch member 106, such as at the distal end, suitably in registry with the side-branch stent 112. The side-branch balloon catheter 406 may then be releasably attached to the side-branch member 106. With the side-branch balloon catheter 406 releasably attached to the side-branch member 106, the side-branch balloon catheter 406 in cooperation with polytetrafluoroethylene film or any suitable mechanism may be used to evert the side-branch member 106 within the main member 104. A side-branch guidewire 410 placed within the guidewire lumen of the side-branch balloon catheter 406 may also be included.

In yet another alternative embodiment, a guiding catheter, or a deployment tube similar to a guiding catheter, may be placed coaxially within the side-branch member 106 in lieu of the 1.2 mm diameter rod. If the side-branch member 106 is equipped with the side-branch stent 112, the guiding catheter or tube may be positioned such that its distal end abuts the proximal end of the side-branch stent 112. When so positioned, the side-branch stent 112 may be configured with an inner diameter approximately equal to that of the guiding catheter or deployment tube. In such an arrangement, the guiding catheter or deployment tube may provide a well-defined passageway for other devices and may aid in the extension of the side-branch member 106. Alternatively, with the guiding catheter or deployment tube positioned as described, the distal end may be releasably attached to the graft component, for example by an adhesive, thermal bond, or other suitable method.

Regardless of how the guiding catheter or tube is positioned within the side-branch member 106, once it is in the desired location, the process of everting the side-branch member into the main member may be completed by using the guiding catheter or tube in cooperation with polytetrafluoroethylene film or any suitable mechanism. If additional support is required during eversion, a rod for example may be placed within the guiding catheter or tube. Once the eversion process is completed, other devices may be placed within the guiding catheter or tube or within the side-branch member 106.

The prosthetic conduit 102 may further be equipped with additional delivery system and/or deployment system components, or may otherwise be prepared for delivery and deployment. For example, the side-branch balloon catheter 406 may be inserted coaxially within the distal end of the side-branch member 106 and releasably attached to the side-branch member 106. Further, the prosthetic conduit 102 may receive the main balloon catheter 400 or be placed within a constraining sheath 902. For example, the prosthetic conduit 102 may be suitably folded into a compact configuration and placed in a constraining sheath 902. The push tube 900 may then be placed within the constraining sheath 902. If required, the side-branch balloon 406 may be removed during the folding process, and repositioned when convenient. Any suitable arrangement of a constraining sheath 902, push tube 900, side-branch balloon 406, and other components may be employed. In some embodiments, particularly if the push tube 900 is adapted to extend within the main member 104, the prosthetic conduit 102 and the push tube 900 may be arranged prior to placement within the constraining sheath 902.

The various embodiments of the present invention may be delivered and installed by any known method, using any combination of devices. For example, the delivery system may comprise any combination of suitable introducer sheaths, guidewires, balloon catheters, guiding catheters, deployment tubes, constraining sleeves, push tubes, and/or any other accessory in any suitable arrangement.

Example

To demonstrate the characteristics of a preferred embodiment of a circumferentially distensible tube, a 1.2 mm inner diameter film-tube was created using essentially the same process as described above. A 230×45 mm rectangular piece was cut from Solupor 7P03A microporous polyethylene film and wrapped around the circumference of a 4 mm outer diameter stainless steel mandrel. With the wrapping complete, both ends of the 230 mm long wrapped film section were secured to the mandrel with wire. Porous polytetrafluoroethylene film was helically wrapped over the 230 mm long wrapped film section, covering the section entirely. The 4 mm mandrel was then placed in an air convection oven set at 143° C. for 7.5 minutes and subsequently removed and allowed to cool. Once cool, the helically wrapped porous polytetrafluoroethylene film as well as the securing wire were removed and discarded. The resulting 4 mm inner diameter polyethylene tube was then removed from the 4 mm outer diameter mandrel and cut into two equal lengths.

Next, pen marks were placed on one of the 4 mm inner diameter film-tubes, and the film-tube was secured to a sliding mandrel mechanism. In this instance, the sliding mandrel mechanism had a 1.1 mm diameter rod. The entire assembly was heated in an air convection oven set at 150° C. for one minute, and the film-tube was then carefully stretched until the interval between the two pen marks (originally spaced at 70 mm) was approximately 141 mm. The stretching caused the film-tube to reduce in diameter, substantially contacting the 1.1 mm rod. The film-tube was then allowed to cool and removed from the sliding mandrel mechanism.

The film-tube was then manually distended over 3.8 and 4 mm outer diameter tapered mandrels. The approximate lengths separating the two pen marks on the film-tube while on the 3.8 and 4 mm outer diameter tapered mandrels were 85 and 80 mm respectively. With the distention completed, and the film-tube removed from the 4 mm tapered mandrel, the film-tube was secured to the linear slide and stretched until the distance between the two pen marks was approximately 154 mm. With the stretching complete, the film-tube was allowed to remain clamped within the linear slide mechanism for at least of 5 minutes at ambient temperature.

The film-tube was then manually fitted coaxially over a 1.2 mm diameter stainless steel rod. The processing of the film-tube was then completed following the steps as previously described. As previously discussed, the small corrugations were formed within the finished tube, tending to allow the tube to be bent without kinking. Additionally, the completed film-tube was readily circumferentially distensible without significant length change (foreshortening) and without significant diameter change post distention (recoil). The 1.2 mm inner diameter film-tube was capable of circumferential distention to an inner diameter of approximately 4 mm.

To provide comparative data, a nondistensible film-tube was created. The nondistensible film-tube was made with approximately the same number of film layers and the same film used to make the 1.2 mm circumferentially distensible film-tube above, but was not processed to render it circumferentially distensible or to exhibit enhanced flexibility.

More particularly, a 200×17 mm rectangular piece of Solupor 7P03A microporous polyethylene film was cut and wrapped around the circumference of a 1.5 mm diameter stainless steel rod. In this case, the circumference of the 1.5 mm rod was approximately 4.7 mm, so to achieve an approximate film thickness of three layers after wrapping, one side of the rectangular piece was cut to a dimension of 17 mm, providing approximately 3 mm extra film length for overlap. With the wrapping complete, both ends of the 200 mm long wrapped film section were secured to the rod with wire and the section was helically wrapped with porous polytetrafluoroethylene film. The 1.5 mm rod was then placed in an air convection oven set at 143° C. for 3 minutes and subsequently removed and allowed to cool. Once cool, the helically wrapped porous polytetrafluoroethylene film as well as the securing wire were removed and discarded. The 1.5 mm inner diameter polyethylene tube was then removed from the 1.5 mm diameter rod. The 1.5 mm inner diameter polyethylene film-tube did not possess any significant circumferential distensibility, nor did it possess any enhanced flexibility. If desired, however, enhanced flexibility may be imparted to such non-distensible tubes by following process steps similar to those previously described for helically wrapping, warming, and longitudinal compression.

The distensibility characteristics for the distensible and the non-distensible tube were measured for comparison. A 16.5 mm long section was cut from the 1.2 mm inner diameter circumferentially distensible film-tube. The section was distended slightly by fitting it coaxially over a 1.5 mm diameter rod. The 16.5 mm long section of tube was then coaxially fitted over an angioplasty balloon with a nominal length of 15 mm, and a nominal diameter of 4 mm. The distention of the tube to a 1.5 mm inner diameter was required so that the tube could be easily placed onto the uninflated balloon without any change in length. Also, a length of 16.5 mm was utilized so as to cover the entire working length of the balloon such that the balloon edges (shoulders) did not inflate at a faster rate than the center. Inflation of the shoulders at a faster rate than the balloon center causes the shoulders at each end of the balloon to bulge and longitudinally compress the length of tube. Such longitudinal compression not only changes the length, but also changes the distensibility characteristics of the tube. This adverse interaction is caused by a mismatch between the length of the balloon and the length of the tube being distended by the balloon. Thus, a length of 16.5 mm successfully matched the tube length to the balloon length and avoided such adverse interactions.

With the tube fitted coaxially onto and centered along the length of the uninflated balloon, digital calipers were used to measure the outer diameter of the tube. The balloon was then inflated at ambient temperature using a hand-held inflation device in approximately 0.1 MPa (1 atm) increments and the outer diameter of the tube was measured at each increment until a pressure of 1.6 MPa (16 atm) was achieved. Once the 1.6 MPa inflation pressure was achieved and the final outer diameter measurement was completed, the balloon was deflated and the length of the tube was measured again using digital calipers.

The difference between the length of the tube prior to distention and the length of the tube after distention is the amount of foreshortening undergone by the tube. The balloon was carefully repacked into the protective packaging sleeve that was provided by the manufacturer and the same test procedure and data collection were repeated on the 1.5 mm non-distensible tube. The recorded outer diameter data were used to create a plot (FIG. 15) of tube outer diameter as a function of inflation pressure.

FIG. 15 shows a plot of tube outer diameter as a function of inflation pressure for both the distensible and the non-distensible tube. The distensible tube generally increases in diameter with increasing inflation pressure. The diameter increase tends to reduce once the tube has reached outer diameters above approximately 3.75 mm, signifying that the tube is approaching the maximum amount of distention that can be achieved without the application of extremely high inflation pressures. The distensible tube reaches an outer diameter of approximately 4 mm under 1.6 MPa (16 atm) inflation pressure.

FIG. 15 includes outer diameter data for the balloon catheter only. These data are provided within the instructions for use of the balloon catheter, and are included in FIG. 15 to show that the outer diameter of the balloon catheter alone (as a function of inflation pressure) is greater than that of the distensible tube during distention by the balloon catheter. Thus, the distensible tube is limiting the outer diameter of the balloon catheter during inflation. Note that the data provided within the instructions for use of the balloon catheter range only from 0.2 to 1.6 MPa (2 to 16 atm). FIG. 15 also shows the distensibility characteristics of the non-distensible tube. The diameter of the non-distensible tube remains fairly constant and is relatively unchanged by the inflation pressure imparted to it via the balloon catheter.

Prior to distention, as stated above, the length of the distensible tube was 16.5 mm. The length of the distensible tube after distention was measured to be approximately 15.7 mm, resulting in approximately 0.8 mm of foreshortening. Dividing the 0.8 mm foreshortening value by the 16.5 mm length prior to distention, and converting to a percentage yields a foreshortening percentage of approximately 4.8 percent. Similarly, the length of the non-distensible tube after distention (although the tube did not actually undergo a substantial change in diameter) was measured to be 16.1 mm, yielding a foreshortening value of 0.4 mm or approximately 2.4 percent. In the case of the non-distensible tube, the change in length was apparently due primarily to the shoulders of the balloon bulging against the ends of the tube and causing the slight length reduction.

To determine the recoil characteristics of the distensible 1.2 mm inner diameter tube, the tube was carefully fitted over a 1.5 mm diameter rod, causing a 25% increase in diameter. The tube was then removed from the rod and left undisturbed for 30 minutes. After the passing of 30 minutes, the tube was pushed back onto the 1.5 mm rod by carefully grasping one end of the tube and pushing the other end of the tube onto the rod. An approximately 6 mm length of tube was pushed onto the 1.5 mm diameter rod before the tube buckled and could be pushed onto the rod no further. Because the tube could be fitted onto the 1.5 mm rod at least partially, there is indication of little to no recoil (or change in diameter).

The same tube is then studied for flexibility or kink resistance. The tube was carefully wrapped around the circumference of an 11 mm outer diameter mandrel with no indication of gross buckling of the tube. The tube was then released from the mandrel, and rather than returning to its original substantially straight configuration, it remained curved, in a semicircular shape having a radius of approximately 15 mm. To provide comparative data, a length of the 1.5 mm non-distensible tube was wrapped around the circumference of the same 11 mm outer diameter mandrel. The non-distensible tube exhibited various points where kinking (gross buckling) occurred. When released from the mandrel, the non-distensible tube returned to a substantially straight configuration.

To further demonstrate the recoil characteristics of the distensible 1.2 mm inner diameter tube, a new length of tube was tested, in a manner similar to that described above. In this case, rather than distending the tube 25%, a length of the tube was distended over the 4 mm tapered mandrel. The tube was then removed from the tapered mandrel and left undisturbed for 30 minutes. After 30 minutes, attempts were made to push the tube onto a 4 mm (non-tapered) mandrel by carefully grasping the undistended end of the tube and pushing the distended end of the tube onto the mandrel. The tube, however, having undergone some recoil, did not fit onto the 4 mm mandrel.

Similar attempts were then made to coaxially fit the tube onto a 3.8 mm (non-tapered) mandrel. The section of the tube, which was distended to a 4 mm inner diameter, fit over the 3.8 mm mandrel easily, indicating that the inner diameter of the tube was then approximately 3.8 mm. Thus, the distended diameter of the tube was 4 mm and the recoil diameter of the tube was approximately 3.8 mm, resulting in a recoil value of approximately 0.2 mm. Dividing the approximate recoil value of 0.2 mm by the distended diameter of 4 mm, and converting to a percentage yields a percent recoil value of approximately 5 percent.

Accordingly, a prosthetic conduit according to various aspects of the present invention may be suitable for the treatment of both aneurysmal and occlusive vascular disease within coronary and peripheral blood vessels, as well as within the neurovasculature, and various other bodily conduits. The prosthetic conduit facilitates endoluminally treating aneurysmal vessels while maintaining normal blood flow to a side-branch vessel originating along the length of the aneurysm. Thus, the prosthetic conduit tends to alleviate the potential for ischemic complications in other bodily locations, and also tends to inhibit the situation of retrograde blood flow through the side-branch vessel, facilitating the aneurysm exclusion process. The prosthetic conduit also provides, by virtue of the graft material, a physical barrier that impedes reproliferation of disease into the lumen of the treated blood vessel. Moreover, the prosthetic conduit provides a preformed bifurcated junction, obviating highly accurate placement as required during the formation of a bifurcation using two stents. The prosthetic conduit including the main member and side-branch member grafts also tends to control redistribution of plaque at the side-branch and reduce the chance of inadvertent blockage due to plaque movement.

In accordance with various other aspects of the present invention, the prosthetic conduit provides several advantages and characteristics. For example, such a prosthetic conduit may allow relative ease of sizing, and may accommodate a range of main and side-branch vessel diameters. The prosthetic conduit may also offer a high degree of flexibility, bending substantially without kinking, and thus having the ability to conform to a variety of bifurcation geometries. Additionally, the prosthetic conduit may be installed through a singular vascular access site. Also, the prosthetic conduit may include radiopaque markers, or may be at least partially constructed of materials that are easily visualized radiographically, facilitating the installation process. The prosthetic conduit may also be installed utilizing conventional, non-specialized tools and devices for vascular surgery, interventional radiology, interventional cardiology, and the like.

The present invention has been described above with reference to various preferred embodiments. However, changes and modifications may be made to various exemplary embodiments without departing from the scope of the present invention. For example, various combinations of the main members 104 and one or more side-branch members 106 may be provided. Further, various changes in the configurations of the main member 104 and the side-branch member 106, for example various combinations of stents and grafts and various materials, may be provided. These and other changes or modifications are intended to be included within the scope of the present invention as set forth in the appended claims.

What is claimed is:

1. A method for making a conduit, comprising:
   providing on one of a mandrel and a rod an underlayer;
   bonding a plurality of layers including a least one layer of a polyethylene material to form a tube while the plurality of layers are positioned over the underlayer;
   treating the tube at least one of thermally and physically to provide the tube with desired characteristics;
   removing the underlayer from under the tube; and
   removing the tube from the one of the mandrel or the rod;
   wherein the underlayer comprises a film helically wrapped about the one of the mandrel and the rod and the step of removing the underlayer from under the tube comprises pulling a free end of the underlayer from under the tube.

2. The method as recited in claim 1, wherein the film comprises a polytetrafluoroethylene film.

3. The method as recited in claim 1, wherein the tube is at least one of thermally and physically treated to provide the tube itself with enhanced flexibility and kink resistance whereupon a bending of the tube will show no visible indication of gross buckling of the tube.

4. The method as recited in claim 1, wherein the tube is at least one of thermally and physically treated to render at least a portion of the tube itself distensible with minimal foreshortening and recoil.

5. The method as recited in claim 1, comprising treating the tube to provide for elution of a drug.

6. The method as recited in claim 1, comprising treating the tube to provide for regulation of cell growth and division.

7. The method as recited in claim 1, comprising applying a biocompatible coating to the tube.

8. The method as recited in claim 1, comprising associating the tube with a stent frame after removing the tube from the one of the mandrel or the rod.

9. The method as recited in claim 1, comprising treating the tube to render at least a portion of the tube radioactive.

10. The method as recited in claim 1, comprising treating the tube to render at least a portion of the tube radiopaque.

11. A method for making a conduit, comprising:
    providing on one of a mandrel and a rod an underlayer;
    bonding a plurality of layers to form a tube while the plurality of layers are positioned over the underlayer;
    treating the tube at least one of thermally and physically to provide the tube with desired characteristics;
    removing the underlayer from under the tube; and
    removing the tube from the one of the mandrel or the rod;
    wherein each of the plurality of layers comprises a biocompatible material, the underlayer comprises a film helically wrapped about the one of the mandrel and the rod, and the step of removing the underlayer from under the tube comprises pulling a free end of the underlayer from under the tube.

12. The method as recited in claim 11, wherein the biocompatible material of each of the plurality of layers is selected from a group consisting of a polyester material, a polyether sulfone material, a polyethylene material, a polytetrafluoroethylene material, and a polyurethane material.

13. The method as recited in claim 11, wherein the film comprises a polytetrafluoroethylene film.

14. The method as recited in claim 11, wherein the tube is at least one of thermally and physically treated to provide the tube itself with enhanced flexibility and kink resistance whereupon a bending of the tube will show no visible indication of gross buckling of the tube.

15. The method as recited in claim 11, wherein the tube is at least one of thermally and physically treated to render at least a portion of the tube itself distensible with minimal foreshortening and recoil.

16. The method as recited in claim 11, comprising treating the tube to provide for elution of a drug.

17. The method as recited in claim 11, comprising treating the tube to provide for regulation of cell growth and division.

18. The method as recited in claim 11, comprising applying a biocompatible coating to the tube.

19. The method as recited in claim 11, comprising associating the tube with a stent frame after removing the tube from the one of the mandrel or the rod.

20. The method as recited in claim 11, comprising treating the tube to render at least a portion of the tube radioactive.

21. The method as recited in claim 11, comprising treating the tube to render at least a portion of the tube radiopaque.

* * * * *